(12) United States Patent
Gregg et al.

(10) Patent No.: US 10,812,426 B1
(45) Date of Patent: Oct. 20, 2020

(54) DATA DERIVED USER BEHAVIOR MODELING

(71) Applicant: C/HCA, Inc., Nashville, TN (US)

(72) Inventors: William Michael Gregg, Nashville, TN (US); Jim Najib Jirjis, Nashville, TN (US); Jonathan Perlin, Nashville, TN (US); Christopher Mason, Nashville, TN (US)

(73) Assignee: C/HCA, Inc., Nashville, TN (US)

(*) Notice: Subject to any disclaimer, the term of this patent is extended or adjusted under 35 U.S.C. 154(b) by 0 days.

(21) Appl. No.: 16/545,122

(22) Filed: Aug. 20, 2019

Related U.S. Application Data

(63) Continuation of application No. 16/181,226, filed on Nov. 5, 2018, now Pat. No. 10,412,028, which is a continuation-in-part of application No. 15/917,446, filed on Mar. 9, 2018, and a continuation-in-part of application No. 15/620,607, filed on Jun. 12, 2017, now Pat. No. 10,121,389, which is a continuation of application No. 14/287,408, filed on May 27, 2014, now Pat. No. 9,715,835.

(60) Provisional application No. 62/470,672, filed on Mar. 13, 2017, provisional application No. 61/827,466, filed on May 24, 2013.

(51) Int. Cl.
*H04L 12/58* (2006.01)
*G16H 50/30* (2018.01)
*A61B 5/00* (2006.01)

(52) U.S. Cl.
CPC .......... *H04L 51/046* (2013.01); *A61B 5/0022* (2013.01); *G16H 50/30* (2018.01)

(58) Field of Classification Search
None
See application file for complete search history.

(56) References Cited

U.S. PATENT DOCUMENTS

| | | |
|---|---|---|
| 6,269,339 B1 | 7/2001 | Silver |
| 7,254,628 B2 | 8/2007 | Koops et al. |
| 7,263,551 B2 | 8/2007 | Belfiore et al. |
| 7,509,263 B1 | 3/2009 | Fiedotin et al. |
| 7,519,826 B2 | 4/2009 | Carley |
| 7,587,368 B2 | 9/2009 | Felsher |
| 7,757,268 B2 | 7/2010 | Gupta et al. |
| 8,010,385 B1 | 8/2011 | Henderson et al. |
| 8,042,158 B2 | 10/2011 | Larsen |
| 8,235,724 B2 | 8/2012 | Gilley et al. |
| 8,291,468 B1 | 10/2012 | Chickering |

(Continued)

OTHER PUBLICATIONS

Non-Final Office Action dated Feb. 5, 2020 in related U.S. Appl. No. 15/917,446, all pgs.

(Continued)

*Primary Examiner* — Joshua Joo
(74) *Attorney, Agent, or Firm* — Kilpatrick Townsend & Stockton, LLP

(57) ABSTRACT

In some examples, user models are generated to represent experience of users with respect to their roles. Models that represent conditions are also generated. As part of generating a support element for a particular user, a triggering event is detected (e.g., an update to a user record), a condition is identified, a condition model and a user model are compared to identify a condition preparedness score. This score is used to generate the support element, which is shared with a user device of the user.

20 Claims, 14 Drawing Sheets

(56) References Cited

U.S. PATENT DOCUMENTS

| | | | |
|---|---|---|---|
| 8,566,115 | B2 | 10/2013 | Moore |
| 8,595,792 | B2 | 11/2013 | Azagury et al. |
| 8,600,777 | B2 | 12/2013 | Schoenberg et al. |
| 8,600,895 | B2 | 12/2013 | Felsher |
| 8,781,855 | B2 | 7/2014 | Miller et al. |
| 8,949,137 | B2 | 2/2015 | Crapo et al. |
| 9,069,984 | B2 | 6/2015 | Said et al. |
| 9,158,932 | B2 | 10/2015 | Ritter et al. |
| 9,202,084 | B2 | 12/2015 | Moore |
| 9,281,993 | B2 | 3/2016 | Kaminsky et al. |
| 9,391,973 | B2 | 7/2016 | Fischer et al. |
| 9,613,190 | B2 | 4/2017 | Ford et al. |
| 9,710,600 | B1 | 7/2017 | Dunleavy et al. |
| 9,715,835 | B2 | 7/2017 | Mason et al. |
| 9,762,553 | B2 | 9/2017 | Ford et al. |
| 9,779,407 | B2 | 10/2017 | Adjaoute |
| 9,787,685 | B2 | 10/2017 | Zhang et al. |
| 9,905,112 | B1 | 2/2018 | Krayer et al. |
| 9,973,455 | B1 | 5/2018 | Fowler et al. |
| 10,027,653 | B2 | 7/2018 | Kim |
| 10,033,702 | B2 | 7/2018 | Ford et al. |
| 10,121,389 | B1 | 11/2018 | Mason et al. |
| 10,140,421 | B1 | 11/2018 | Bernard |
| 10,324,947 | B2 * | 6/2019 | Dey ................ G06N 20/00 |
| 10,325,070 | B2 | 6/2019 | Beale et al. |
| 10,412,028 | B1 | 9/2019 | Gregg et al. |
| 2001/0051765 | A1 * | 12/2001 | Walker ............ A61B 5/4839 600/300 |
| 2004/0247748 | A1 | 12/2004 | Bronkema |
| 2005/0228691 | A1 | 10/2005 | Paparo |
| 2006/0112050 | A1 * | 5/2006 | Miikkulainen ...... G16H 50/20 706/46 |
| 2007/0179351 | A1 | 8/2007 | Kil et al. |
| 2008/0040160 | A1 | 2/2008 | Scherpbier et al. |
| 2008/0076637 | A1 | 3/2008 | Gilley |
| 2008/0094207 | A1 | 4/2008 | Collins et al. |
| 2008/0097792 | A1 | 4/2008 | Marge |
| 2009/0043634 | A1 | 2/2009 | Tisdale |
| 2009/0106225 | A1 | 4/2009 | Smith |
| 2010/0161353 | A1 | 6/2010 | Mayaud |
| 2011/0320221 | A1 * | 12/2011 | Duffey-Rosenstein ............... G06Q 50/22 705/3 |
| 2012/0035959 | A1 * | 2/2012 | Berdia .............. G06F 19/325 705/3 |
| 2012/0173280 | A1 | 7/2012 | Gustafson |
| 2013/0166317 | A1 | 6/2013 | Beardall |
| 2013/0216989 | A1 | 8/2013 | Cuthbert |
| 2014/0045156 | A1 | 2/2014 | Alessandri |
| 2015/0006192 | A1 | 1/2015 | Sudharsan et al. |
| 2015/0052160 | A1 | 2/2015 | Hussam |
| 2016/0174913 | A1 | 6/2016 | Somanath |
| 2016/0342753 | A1 * | 11/2016 | Feazell ............. G16H 10/60 |
| 2018/0046773 | A1 * | 2/2018 | Tang ................ G16H 50/30 |
| 2018/0181716 | A1 | 6/2018 | Mander et al. |

OTHER PUBLICATIONS

Non-Final Office Action, dated Aug. 23, 2017 in related U.S. Appl. No. 15/620,607, 11 pgs.

Notice of Allowance, dated Jul. 2, 2018 in related U.S. Appl. No. 15/620,607, 9 pgs.

Non-Final Office Action dated May 13, 2015 in related U.S. Appl. No. 14/287,408, 21 pgs.

Final Office Action, dated Nov. 10, 2015 in related U.S. Appl. No. 14/287,408, 7 pgs.

Notice of Allowance, dated Mar. 10, 2017 in related U.S. Appl. No. 14/287,408, 6 pgs.

Advisory Action, dated Feb. 3, 2016 in related U.S. Appl. No. 14/287,408, 4 pgs.

Non-Final Office Action, dated Mar. 4, 2016 in related U.S. Appl. No. 14/287,408, 16 pgs.

Final Office Action dated Nov. 18, 2016 in related U.S. Appl. No. 14/287,408, 7 pgs.

Notice of Allowance dated May 1, 2019 in related U.S. Appl. No. 16/181,226, all pgs.

First Action Interview Pilot Program Pre-Interview Communication dated Mar. 5, 2019 in related U.S. Appl. No. 16/181,226, 6 pgs.

Final Office Action dated Sep. 4, 2020 in related U.S. Appl. No. 15/917,446, all pgs.

* cited by examiner

1016

```
                    DR. WILSON
      ┌ SPECIALTY: GENERALIST
      │ YEARS IN PRACTICE: 12
1202 ─┤ . . .
      └ LOCATION: SEATTLE, WA
      ┌ CONDITION FREQUENCY (#/PERIOD):
      │     COMMON COLD – 400
      │     FLU – 200
      │     . . .
      │     HYPERGLYCEMIA – 20
      │ CONDITION SEVERITY (SCORE 1-100)
      │     COMMON COLD – 10/100
1204 ─┤     FLU – 25/100
      │     . . .
      │     HYPERGLYCEMIA – 35/100
      │ OUTCOMES RELATED TO TREATMENT OF CONDITIONS
      │     COMMON COLD
      │     FLU
      │     . . .
      └     HYPERGLYCEMIA
      ┌ SYSTEM DETECTED ACTIVITIES
      │     CME COURSES
      │     ARTICLE READINGS
1206 ─┤
      │     . . .
      └     CONSULTATIONS
```

FIG. 12

DATA DERIVED USER BEHAVIOR MODELING

CROSS-REFERENCE TO RELATED APPLICATIONS

This application is a continuation of U.S. patent application Ser. No. 16/181,226 filed Nov. 5, 2018, and entitled "DATA DERIVED USER BEHAVIOR MODELING," which is a continuation-in-part of U.S. patent application Ser. No. 15/917,446, filed Mar. 9, 2018, and entitled "AUTHORIZED USER MODELING FOR DECISION SUPPORT," which claims the benefit of priority of U.S. Provisional Application No. 62/470,672, filed Mar. 13, 2017. U.S. patent application Ser. No. 16/181,226 is also a continuation-in-part of U.S. patent application No. U.S. Ser. No. 15/620,607 filed Jun. 12, 2017, issued as U.S. Pat. No. 10,121,389, and entitled "PROGRESSIVE PREGNANCY WELLNESS PROMOTION USING A PROGRESSION SCHEME AND TASK TRACKING," which is a continuation of U.S. patent application Ser. No. 14/287,408, filed on May 27, 2014, issued as U.S. Pat. No. 9,715,835, and entitled "PROGRESSIVE PREGNANCY WELLNESS PROMOTION USING A PROGRESSION SCHEME AND TASK TRACKING," which claims the benefit of priority of U.S. Provisional Application No. 61/827,466, filed on May 24, 2013, entitled "PROGRESSIVE PREGNANCY WELLNESS PROMOTION USING A PROGRESSION SCHEME AND TASK TRACKING." The full disclosures of the above-identified applications are incorporated herein in their entirety.

BACKGROUND

The amount of data generated each day continues to grow. In some environments, some of this data may be stored, while a majority of it may be evaluated and abandoned or ignored. Users and computing devices are beginning to rely more and on this data to make decisions. This may be especially true when the data is introduced as part of an operational flow. However, the time required to sort through stored data can create inefficiencies and the fact that other data may typically be ignored or abandoned may create undesirable outcomes.

BRIEF DESCRIPTION OF THE DRAWINGS

Various examples in accordance with the present disclosure will be described with reference to the drawings, in which:

Various examples in accordance with the present disclosure will be described with reference to the drawings, in which:

FIG. 12 is an example block diagram relating to implementing techniques relating to data derived user behavior modeling, according to at least one example;

SUMMARY

Figure 1:
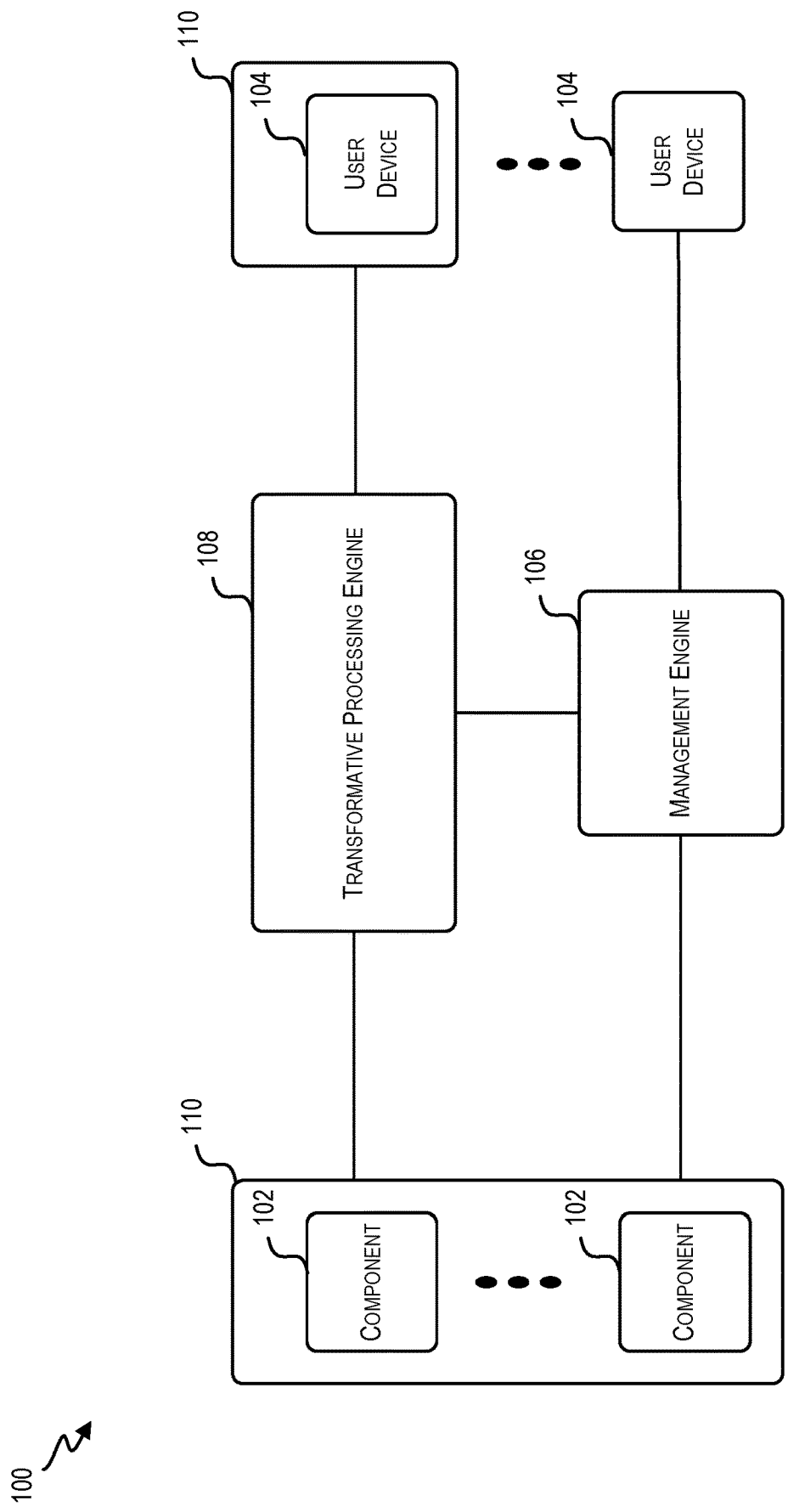
FIG. 1 is an example block diagram illustrating an interaction system in which techniques relating to data derived user behavior modeling may be implemented, according to at least one example.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method, including: accessing a user list to identify a plurality of dependent users. The computer-implemented method also includes analyzing one or more data streams for data that reference individual dependent users of the plurality of dependent users, the one or more data streams extending between a plurality of generation devices and one or more storage devices, at least one data stream including messages of a standardized format. The computer-implemented method also includes for each dependent user of the plurality of dependent users, detecting a triggering event based on monitoring the one or more data streams in accordance with a set of triggering rules, the triggering event including a message that updates a user record associated with a dependent user of the plurality of dependent users; determining a likely present condition of the dependent user based on one or more condition data present in the message or in the user record; selecting a present condition model from a set of present condition models based on the likely present condition; identifying a user model for an authorized user that is associated with the likely present condition of the dependent user; comparing the present condition model with the user model to determine a condition preparedness score for the authorized user; and providing, based on the condition preparedness score, a support element for presentation at a user device associated with the authorized user. Other embodiments of this aspect include corresponding computer systems, apparatus, and computer programs recorded on one or more computer storage devices, each configured to perform the actions of the methods.

Implementations may include one or more of the following features. The computer-implemented method where the support element includes a communication that is customized to a context of the authorized user with respect to the dependent user. The computer-implemented method where the user model includes a plurality of data objects representative of user preparedness for responding to the likely present condition, the plurality of data objects including at least one of a generic data object, an experience data object, or an activity data object. The computer-implemented method where: the generic data object represents generic information of the authorized user. The computer-implemented method here the experience data object represents historical experience the authorized user has obtained by responding to the likely present condition at other times. The computer-implemented method where the activity data object represents additional knowledge the authorized user has obtained that is related to the likely present condition. The computer-implemented method where the experience data object is determined based on one or more historical data including code-based data, note entry data, or placed order data. The computer-implemented method where the present condition model includes a set preparedness indicators indicative of authorized user preparedness for responding to the likely present condition. The computer-implemented method further including: assigning the authorized user to one of a plurality of buckets based on the condition preparedness score, each bucket representing a distinct level of user preparedness for responding to the likely present condition. The computer-implemented method may also include generating the support element based on the assigned bucket. Implementations of the described techniques may include hardware, a method or process, or computer software on a computer-accessible medium.

One general aspect includes a system, including: a memory including computer-executable instructions; and a processor configured to access the memory and execute the computer-executable instruction to perform operations. The operations include accessing a user list to identify a plurality of dependent users. The operations also include analyzing one or more data streams for data that references individual dependent users of the plurality of dependent users, the one or more data streams extending between a plurality of generation devices and one more storage devices, at least one data stream including messages of a standardized format. The operations also include, for each dependent user of the plurality of dependent users, detecting a triggering event based on monitoring the one or more data streams in accordance with a set of triggering rules, the triggering event including a message that updates a user record associated with a dependent user of the plurality of dependent users; determining a likely present condition of the dependent user based on one or more condition data present in the message or in the user record; selecting a present condition model from a set of present condition models based on the likely present condition; identifying a user model for an authorized user that is associated with the likely present condition of the dependent user; comparing the present condition model with the user model to determine a condition preparedness score for the authorized user; and providing, based on the condition preparedness score, a support element for presentation at a user device associated with the authorized user. Other embodiments of this aspect include corresponding computer systems, apparatus, and computer programs recorded on one or more computer storage devices, each configured to perform the actions of the methods.

Implementations may include one or more of the following features. The system where the support element includes a communication that is customized to a context of the user with respect to the dependent user. The system where the one or more condition data reference the likely present condition. The system where the user model includes a plurality of data objects representative of user preparedness for responding to the likely present condition, the plurality of data objects including at least one of a generic data object, an experience data object, or an activity data object. The system where the generic data object represents generic information of the authorized user. The system where the experience data object represents historical experience the authorized user has obtained by responding to the likely present condition at other times. The system where the activity data object represents additional knowledge the authorized user has obtained that is related to the likely present condition. The system where the experience data object is determined based on one or more historical data including code-based data, note entry data, or placed order data. The system where the present condition model includes a set preparedness indicators indicative of user preparedness for responding to the likely present condition. Implementations of the described techniques may include hardware, a method or process, or computer software on a computer-accessible medium.

One general aspect includes a non-transitory computer-readable storage device including computer-executable instructions that, when executed by one or more computer systems, cause the one or more computer systems to perform operations including: accessing a user list to identify a plurality of dependent users. The operations also include analyzing one or more data streams for data that references individual dependent users of the plurality of dependent users, the one or more data streams extending between a plurality of generation devices and one more storage devices, at least one data stream including messages of a standardized format. The operations also include, for each dependent user of the plurality of dependent users, detecting a triggering event based on monitoring the one or more data streams in accordance with a set of triggering rules, the triggering event including a message that updates a user record associated with a dependent user of the plurality of dependent users; determining a likely present condition of the dependent user based on one or more condition data present in the message or in the user record; selecting a present condition model from a set of present condition models based on the likely present condition; identifying a user model for an authorized user that is associated with the likely present condition of the dependent user; comparing the present condition model with the user model to determine a condition preparedness score for the authorized user; and providing, based on the condition preparedness score, a support element for presentation at a user device associated with the authorized user. Other embodiments of this aspect include corresponding computer systems, apparatus, and computer programs recorded on one or more computer storage devices, each configured to perform the actions of the methods.

Implementations may include one or more of the following features. The non-transitory computer-readable storage device where the support element includes a communication that is customized to a context of the user with respect to the dependent user. The non-transitory computer-readable storage device where the user model includes a plurality of data objects representative of user preparedness for responding to the likely present condition, the plurality of data objects including at least one of a generic data object, an experience data object, or an activity data object. The non-transitory computer-readable storage device where the present condition model includes a set preparedness indicators indicative of user preparedness for responding to the likely present condition. The non-transitory computer-readable storage device where the operations further include: assigning the user to one of a plurality of buckets based on the condition preparedness score, each bucket representing a distinct level of user preparedness for responding to the likely present condition. The non-transitory computer-readable storage device where the operations further include generating the support element based on the assigned bucket. The non-transitory computer-readable storage device where the message is associated with information output by a computer application executing on a different user device associated with the dependent user, the computer application configured to interact with a server system to record progression of a different condition associated with the dependent user. Implementations of the described techniques may include hardware, a method or process, or computer software on a computer-accessible medium.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Referring first to FIG. 1, a block diagram of an example of an interaction system 100 is illustrated. Generally, in interaction system 100, data can be generated at one or more system components 102 and/or user devices 104. Management engine 106 can manage the flow of communications within interaction system. Transformative processing engine 108 can receive, intercept, track, integrate, process, and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102, and/or data in a corresponding communication received from a user device.

As another example, a user device 104 can be configured to detect input received at an interface of the device. The input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect input requesting particular data, to generate a request communication (e.g., to be sent to transformative processing engine), to receive the requested data and/or to present the received data.

The depicted engines, devices and/or components can communicate over one or more networks. A network of one or more networks can include a wired network (e.g., fiber, Ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or focus. Exemplary types of facilities include server farm facilities, web-server facilities, data-storage facilities, telecommunication facilities, service facilities, and/or operational facilities. For example, a first facility may include a structure at a first location at which one or more resources (e.g., computational resources, equipment resources, laboratory resources, and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another example, different facilities may include resources of similar or same types but may vary in terms of, for example, accessibility, location, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing, and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client, or receiving a service from the client.

In some examples, one or more components 102 and one or more user devices 104 may communicate with transformative processing engine 108 and management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., management engine 106, an entity device, and/or a user device) and/or locally or remotely stored. In some examples, transformative processing engine 108 receives data in a particular format (e.g., the HL7 format) or conforming to any other suitable format and/or is configured to transform received data to conform to the particular format.

One or more components 102 of facility 110 can include and/or has access to a local or remote memory for storing generated data. In some examples, the data is stored by one or more servers local to facility 110. The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from a component (or facility), the record service can identify a corresponding record and update the record to include the data (or processed version thereof). In some examples, the record service provides data to transformative processing engine 108.

Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private, and/or proprietary network or protocols. The use of one or more private and/or proprietary protocols can promote secure transfer of data.

Figure 2:
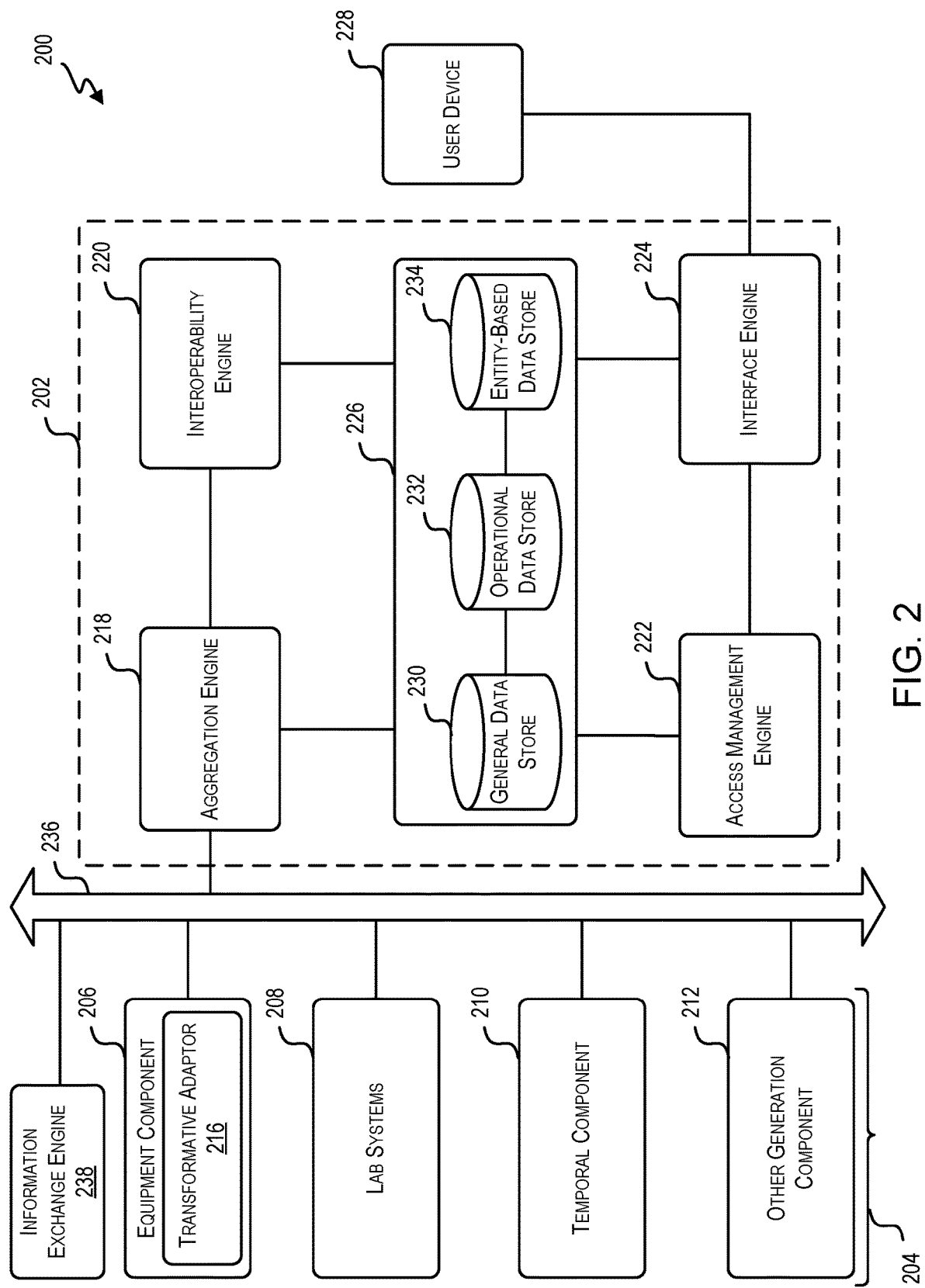
FIG. 2 is an example block diagram illustrating an interaction system in which techniques relating to data derived user behavior modeling may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 include an equipment component 206, a lab systems component 208, a temporal component 210, and other generation component 212. One or more generation components 204 are examples of one or more components 102 discussed with reference to FIG. 1. In some examples, the data may pass to the transformative processing engine 202 via an information exchange service bus 236 (e.g., an enterprise service bus). In some examples, only a portion of the is passed via the information exchange service bus 236, while other portions are passed directly to the transformative processing engine 202 without first passing over the information exchange service bus 236.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design—making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein. In some examples, the generation components 204 provide data to the transformative processing engine 202 via a messaging bus (e.g., an information exchange service bus 236). The messaging bus, which may be included in the transformative processing engine 202 or separate, is able to see data that moves throughout the interaction system 200. The information exchange service bus 236 also includes a subscription registry that can be used to manage subscriptions to the information exchange service bus 236 for certain data (e.g., data having certain characteristics). The information exchange service bus 236 may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Temporal component 210 may include any suitable computing devices used with respect to interaction system 200. For example, temporal component 210 can be configured to allocate a resource to a particular entity during a particular temporal window. Temporal component 210 can monitor a schedule for the resource and can identify one or more available temporal windows that may be secured by a particular entity. Upon receiving an indication, temporal component 210 may update a schedule of a resource to reflect that a particular temporal window is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the location and other details about the component or the user device. In some examples, the component and the user device may include global positioning chips that are configured to determine a geolocation.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine, and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, and the like. Access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized user devices. The information exchange engine 238 is also configured to route inbound messages and route outbound messages, as described herein. The information exchange engine 238 is also configured to generate customized messages based on dependent user data.

Figure 3:
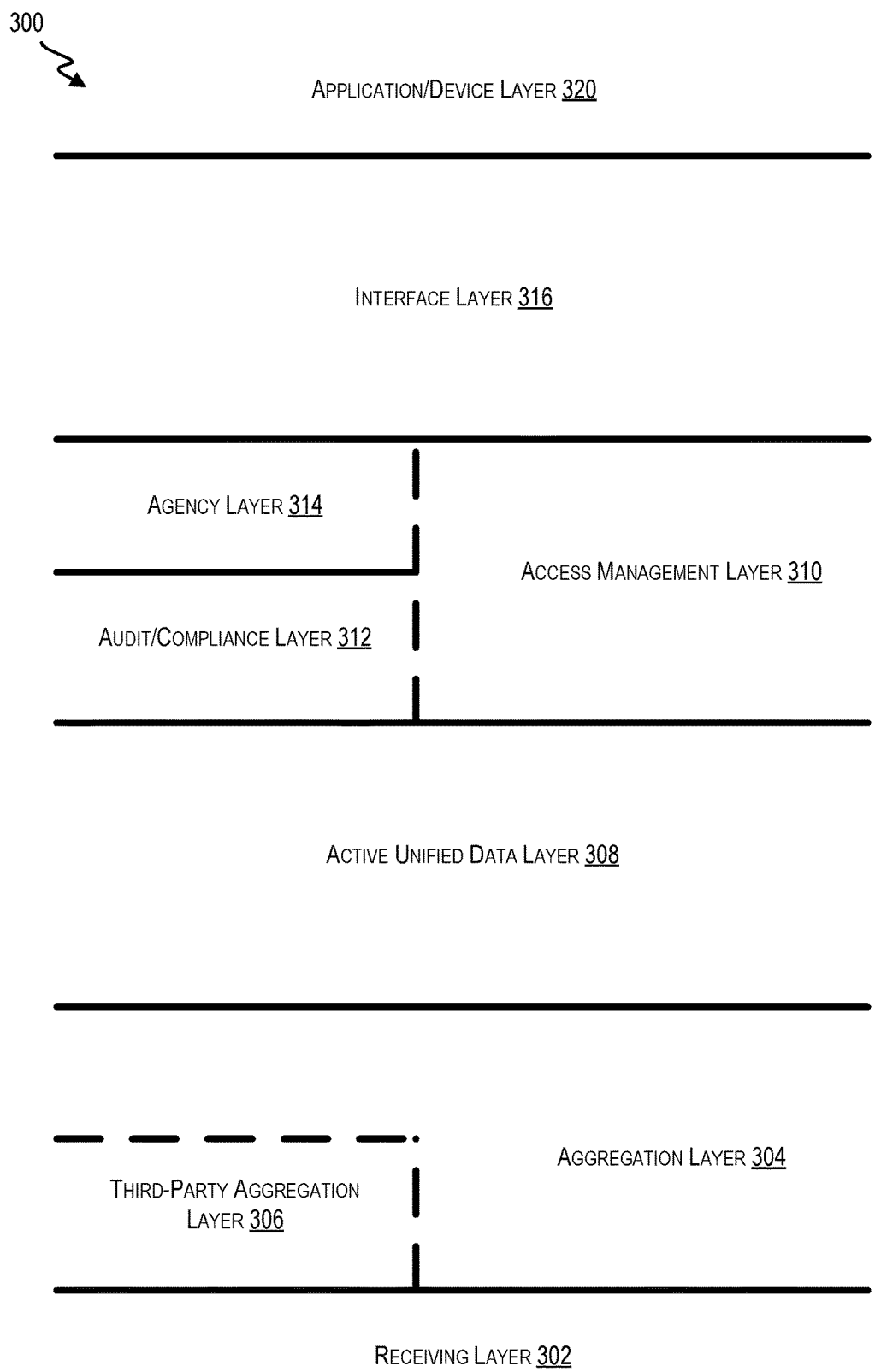
FIG. 3 is an example schematic model illustrating a network communication model in which techniques relating to data derived user behavior modeling may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum, or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties.

Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
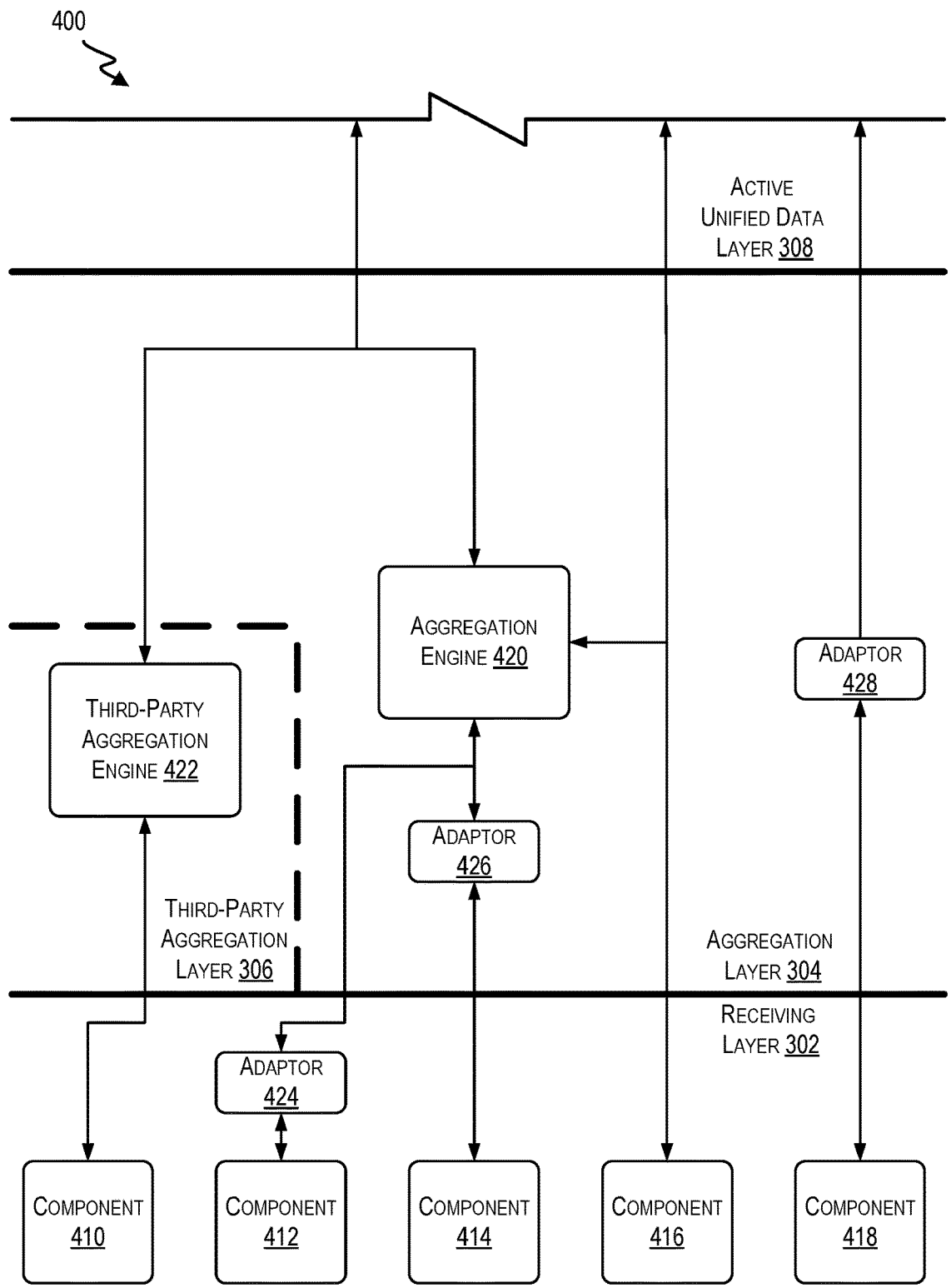
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238. As introduced herein, messages passing through the aggregation layer 304 can pass over the information exchange service bus 236. In this manner, the information exchange engine 238 can access the messages, route the messages, and/or customize the messages.

Figure 5:
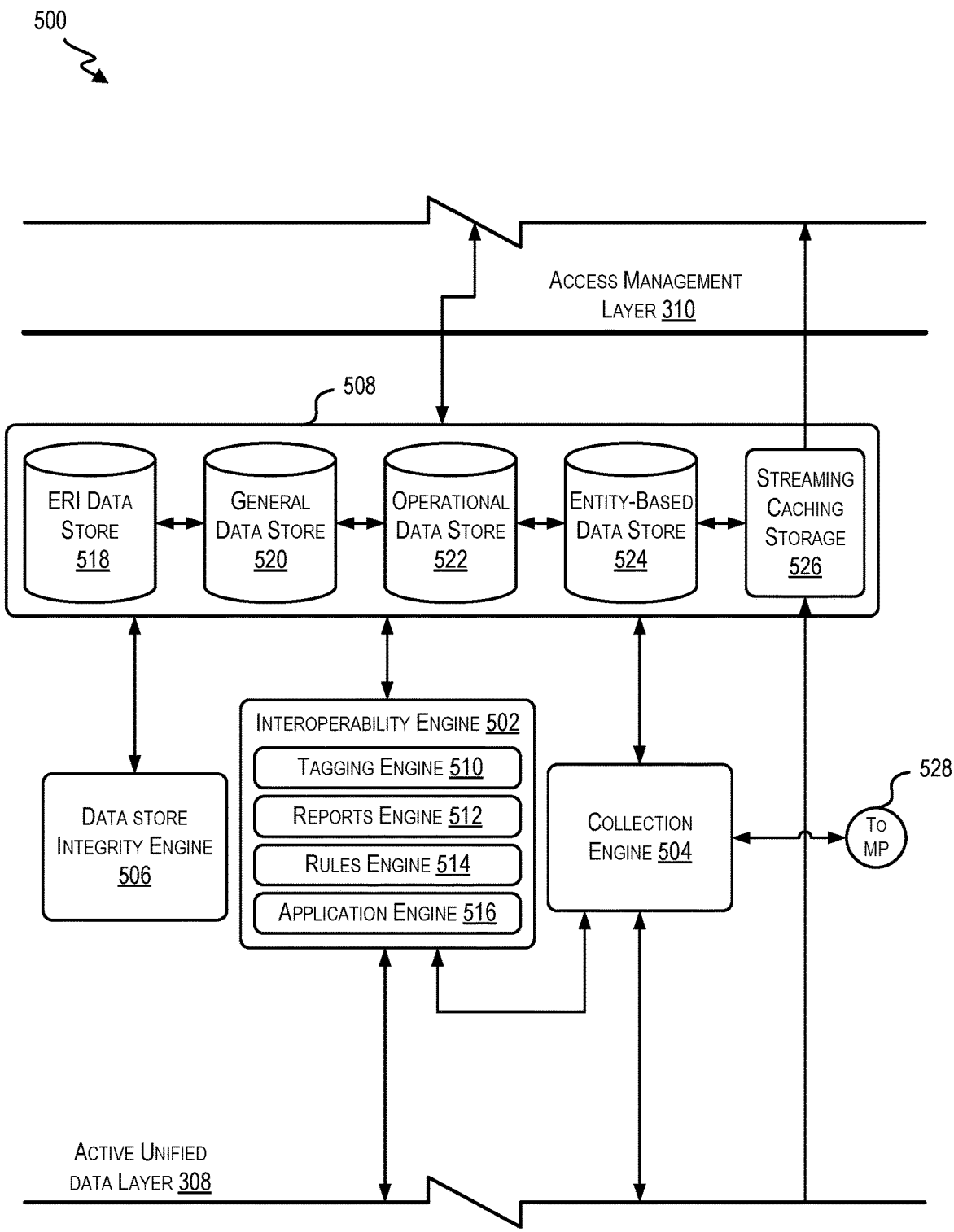
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), management engine 106 (e.g., collection engine 504 of management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to management engine 106 that it saw the message. In this manner, management engine 106 may track messages from end-to-end for the life of the message.

In one example, the messages are requests. The requests may be generated based om user input at one of the components. The requests may be received by transformative processing engine 108 and integrated into the system. In some examples, management engine 106 may be notified that the requests have been received and may therefore be configured to generate message IDs for each request. These message IDs may then be associated with each of the requests. As the requests continue to move throughout the interaction system (e.g., away from transformative processing engine 108), management engine 106 may track their movement using the message IDs. If one of the requests does not arrive at its destination, management engine 106 may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, management engine 106 (e.g., collection engine 504 of management engine 106) may receive the message and/or message identifier directly from one of components 410-418. For example, one of components 410-416 may be configured to generate the unique message identifier and/or communicate directly with management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, collection engine 504 provides unique message identifiers to other elements of the interaction system to monitor the messages as they move throughout the interaction system. Collection engine 504 also provides a portion of the unique message identifiers to a management platform (indicated by a circle 528) for further analysis of the message identifiers. Such analyses may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("ERI data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within ERI record data store 518 is retained data. In some examples, the information within ERI record data store 518 is organized according to entity identifying information. Thus, EM record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. In some examples, the operational data store 522 includes data pertaining to decision making as discussed herein and other data typically used.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
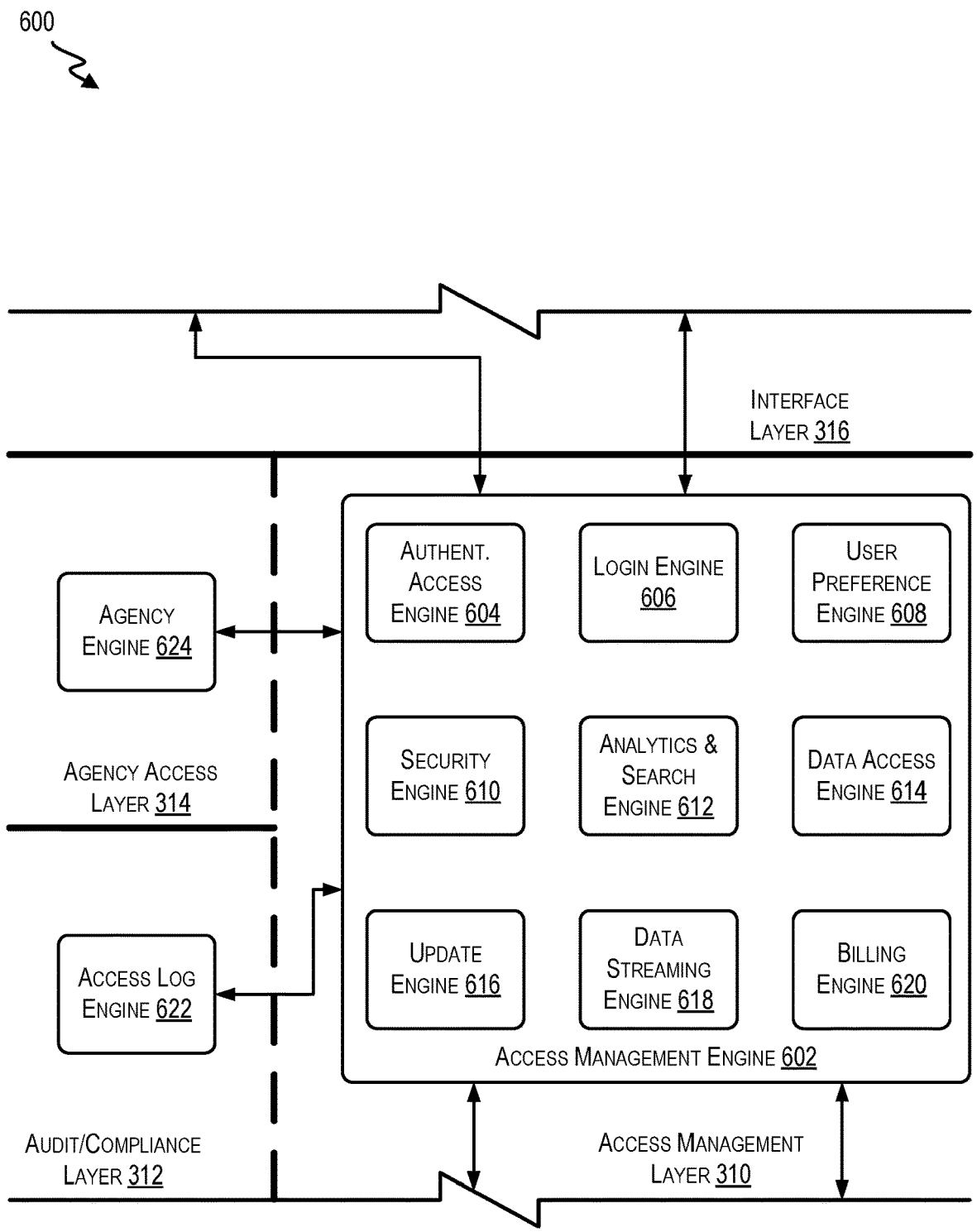
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions, and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. In some examples, agency engine 624 may be used to track one or more performance indicators identified by a government agency and/or to provide report instances of defined types of events. In some examples, a university is an agency that uses agency engine 624 to collect data pertaining to one or more studies. Agency engine 624 can collect the pertinent data, potentially format and/or analyze the data, and facilitate transmission of the data to the appropriate agency.

Figure 7:
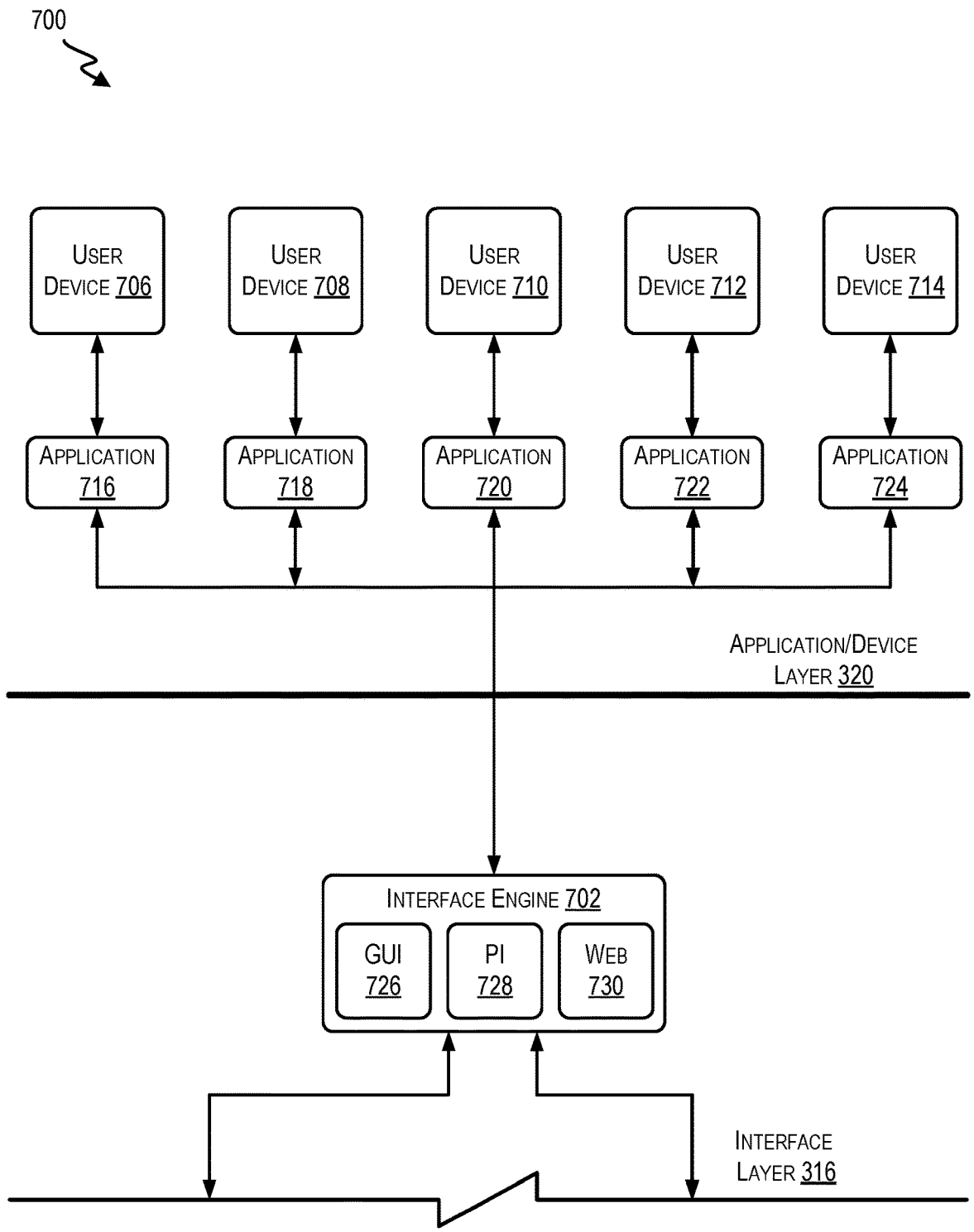
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 706-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for a particular entity. In some examples, application 720 may present different data depending on a focus of the entity and protected information associated with the entity. In this manner, application 720 adapts and automatically adjusts depending on the context in which the entity is using the application. Application 720 may be configured to receive input, adjust presentations, present unprompted alerts, adjust display of content, move more relevant content to the foreground, move less relevant content to the background, and/or populate forms for the entity.

In another example, application 722 may be specific for nurses or types of nurses. In this example, application 722 may include dashboards, widgets, windows, icons, and the like that are customized to individual nurses. Similar to the example discussed above pertaining to the user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data.

In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
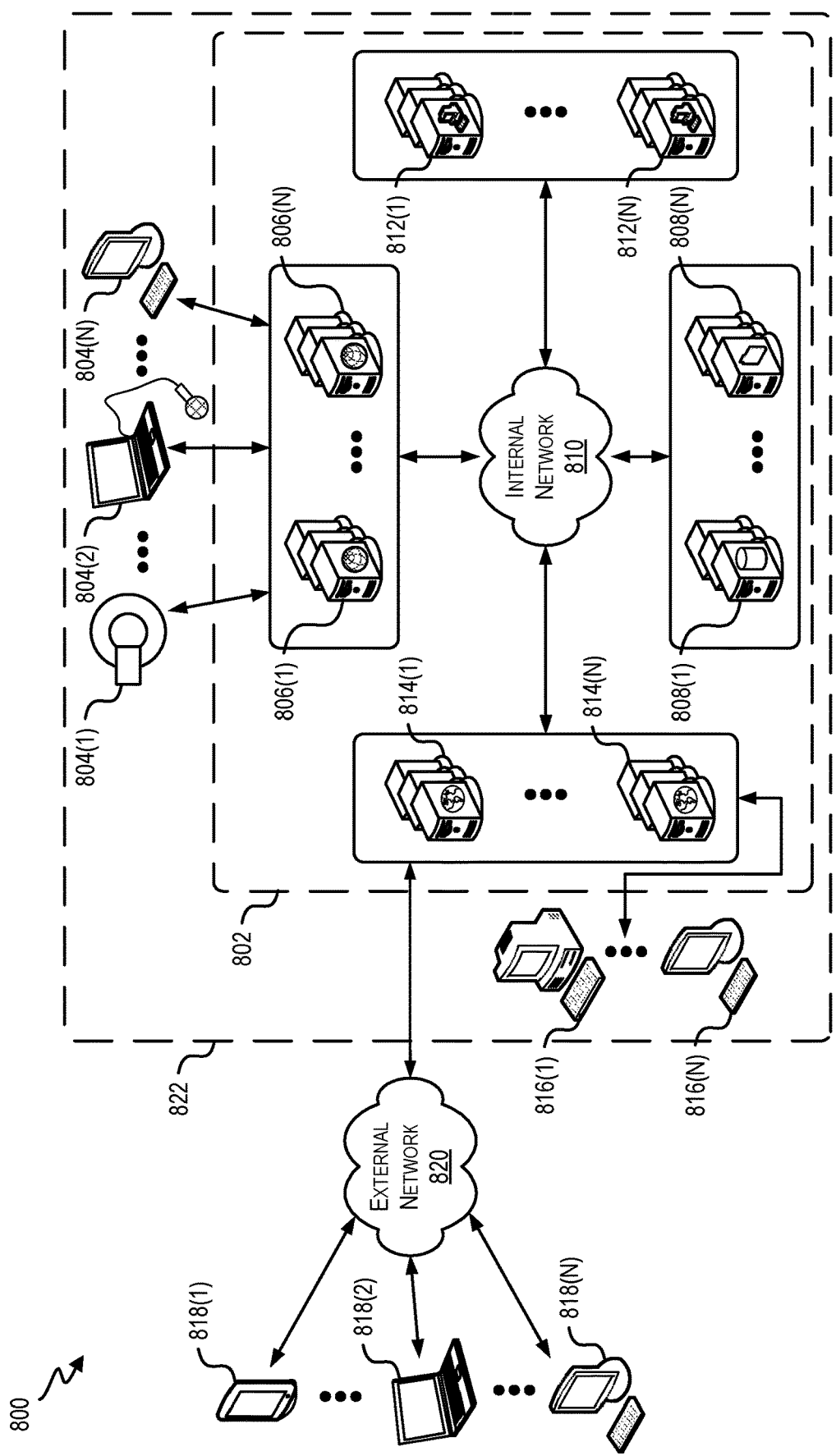
FIG. 8 is an example schematic architecture illustrating an interaction system in which techniques relating to data derived user behavior modeling may be implemented, according to at least one example.

Turning now to FIG. 8, an interaction system 800 is shown according to at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

The systems, processes, and models described with reference to FIGS. 1-8 may be used to implement the techniques described herein with reference to later figures. For example, data communication may be performed within the aggregation layer 304 or the active unified data layer 308. In some examples, messages originate at one of the components 410-418 and are streamed to the data store 508. These messages may be intercepted by the collection engine 504 or any other suitable interceptor device and shared with the authorized user management system described herein.

The techniques described herein relate to techniques for providing tailored support to authorized users to provide guidance in responding to current conditions of dependent users. In one example, an authorized user management system is described. The authorized user management system provides support in the form of tailored decision support output (DSO) to the authorized users (e.g., support elements). DSO comes in many different forms and can be generated and shared with authorized users using different means. In examples described herein, DSO includes jobs, tasks, considerations, suggestions, and the like that relate to responding to current conditions of a dependent user or a group of dependent users. DSO can be introduced into existing workflows of a management system, within a mobile phone application, and/or in any other suitable manner. For example, an example DSO element indicating that an authorized user should consider performing some predefined action with respect to the dependent user can be presented in an application in which the authorized user places typically performs such predefined actions or inputs information about a dependent user's condition (e.g., in a user record). The authorized user management system uses authorized user models (e.g., models that provide a holistic view of the authorized users' experience, education, biases, etc. as they relate to responding to current conditions of dependent users), condition models (e.g., models that represent different conditions and which type of experience, education, etc. is relevant for responding to the different conditions), information about the dependent user (e.g., a likely present condition), and other suitable information to compute a preparedness score that is used to determine whether to generate a DSO element and when to present the DSO element. For example, if the authorized user has considerable experience responding to a certain condition with which a dependent user is currently presented, and the system has not detected that a predefined action relating to responding to the certain condition has been performed, the system may present the DSO element within an application at a user device associated with the authorized user prior to closing the application. In this manner, the DSO element may function as a reminder, but not a strong suggestion. On the other hand, if the authorized user has less experience responding to the certain condition, the system may present the DSO element as a popup immediately when the application is opened. To close out of this popup, the authorized user may be required to engage with the popup in some manner (e.g., click, input data, etc.) to ensure acknowledgement of the DSO element. In some examples, selection of the DSO element enables certain actions to be automatically performed (e.g., automated preparation of documentation necessary for performing the predefined action(s)).

To ensure that DSO is relevant to authorized users, the described system relies on comparison of authorized user models with one or more generic models. The system maintains a set of generic models and individual models for each authorized user. The models begin with basic information (e.g., general experience, experience responding to certain conditions, etc.), but grow as the authorized user performs more activities within the system (e.g., responds to additional conditions, obtains continuing experience, reads articles, etc.). More comprehensive support may be provided to those with a low level of experience; less intrusive support, with fewer limitations and constraints, may be provided to those with a high level of experience. More support in some areas may be provided with experienced authorized users when a particular authorized user needs such guidance. The system also maintains condition models that model conditions to determine support that is related to a particular condition. Based on the condition, the system can compute a condition preparedness score for the authorized user in responding to the condition. The condition preparedness score can be compared to a number of thresholds to determine what support to be shared.

An authorized user management system tracks activities performed by authorized users that impact what, when, and how DSO is presented. The system also tracks how authorized users have responded or otherwise interacted with DSO. Based on this, the system updates the authorized user models and makes the updated authorized user models available for comparison to the condition models. For example, as an authorized user responds to a condition more regularly or assists a dependent user in a manner that results in a positive outcome, the system may update a model for that authorized user with this data. In this manner, the system may base first DSO for identification of a particular condition on a first version of the authorized user model (e.g., prior to assisting the dependent user) and, at a later time, may base second DSO for the identification of the particular condition on a second version of the authorized user model (e.g., after assisting the dependent user). The collection of data and persisting of changings to the authorized user models enables the creation of an end-to-end experience model for the authorized users. Updates may be persisted to the authorized user models at least as often as the authorized users sees dependent users or otherwise interacts with the system. These updates can be performed in real-time to ensure that the models are current.

Use of the authorized user management system improves the functioning of the computer system in which the authorized user management system is implemented. Because the authorized user management engine monitors existing digital messages and does not add traffic to the network, the techniques described herein are implemented without affecting existing bandwidth constraints. Moreover, because the systems and predictive models are trained using the largest and most relevant datasets available (i.e., those maintained in the world's largest clinical data warehouse), the predictions made using the described system are more precise and more accurate than those made by prior art systems trained using smaller datasets. Additionally, because of the quality of the models, fewer computing resources are required to make the predictions as would be required using the prior art systems.

Examples of the disclosure also provide for a number of technical advantages. For example, the disclosure enables operators of networks to offer better customization for their authorized users and for their dependent users, resulting in improved and contextualized care. By implementing the techniques described herein on a centralized server, processing capabilities are freed up on local computing devices (e.g., at record management endpoints). Such centralization also improves the accuracy and precision of the predictive models described herein. For example, because all or almost all messages flow from record management endpoints through the centralized server (e.g., via integration), the predictive models can continuously be updated based on the messages.

Examples described herein provide contextual awareness for authorized users. Support elements are delivered in a ways that are less likely to be interpreted as just noise by the authorized users. The support elements function as a safety net for the authorized users. For example, even experienced authorized users sometimes forget things, and new authorized users may not know what they do not know. The support elements can be used to fill in the gaps.

Example support elements includes an order set and note template list that are specific to an authorized user's specialty, views of data that are customized to the authorized user's specialty, lists of treatment options that are prioritized by specialty—e.g., a first specialist sees certain treatment options at the top, followed by the rest. Different from the a second specialist who sees a different prioritization of treatment options. Other support elements are contemplated besides those previously listed.

The authorized user models can be built over time for each authorized user. As described herein, the authorized user models include contextual details about how often a given authorized user has responded to certain conditions of dependent users, authorized user experience (e.g., attending for 10 years compared to a second year resident), specialty of authorized user (e.g., a first authorized user who has ever responded to a certain condition will receive more detailed support elements than a second authorized user who responds to the certain condition 100 times per year).

Figure 9:
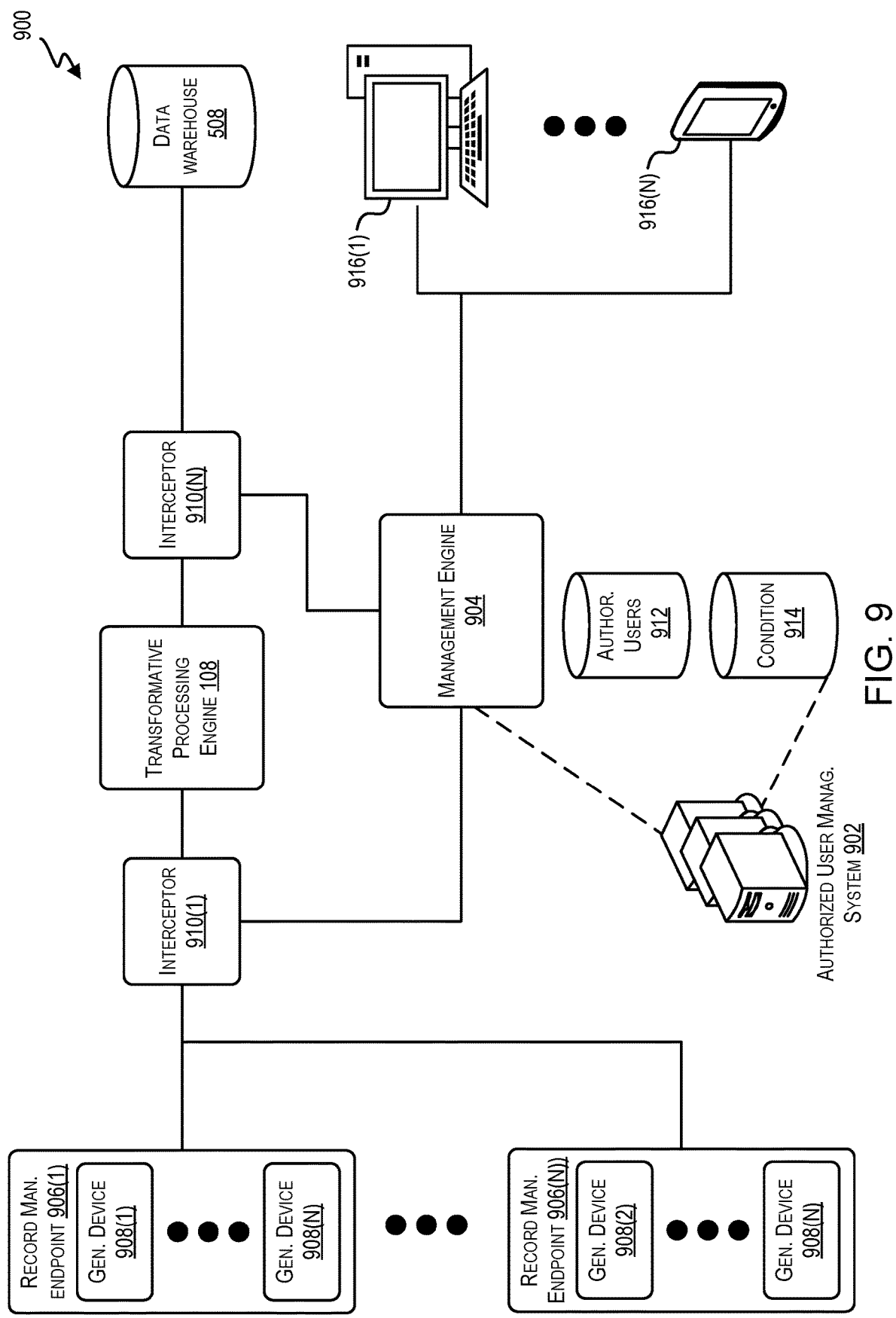
FIG. 9 is an example block diagram illustrating an example architecture in which techniques relating to data derived user behavior modeling may be implemented, according to at least one example.

Turning now to FIG. 9, a management architecture 900 is shown in accordance with at least one example. The management architecture 900 may be implemented using elements of the systems, networks, and models of FIGS. 1-8. For example, the management architecture 900 includes the transformative processing engine 108 and the data warehouse 508, both of which are described in detail herein. The transformative processing engine 108 can process and store data used by an authorized user management system 902 to implement the techniques described herein. For example, the authorized user management system 902, which includes a management engine 904, can access dependent user data, interaction data, feedback data, outcome data, and the like from the transformative processing engine 108 and use such data to evaluate condition models based on authorized user models, update condition models and generic models and authorized user models, and generate DSO. The management engine 904 may include one or more software modules configured to perform the functions described herein with reference to the authorized user management system 902.

The elements of the management architecture 900 may be in network communication via one or more networks (e.g., local, wide area, cellular, broadband, wireless, etc.).

The management architecture 900 includes record management endpoints 906(1)-906(N), e.g., electronic medical record (EMR) platforms. Each record management endpoint 906 can be associated with one or more generation devices 908(1)-908(N). The record management endpoints 906 can be distributed throughout a geographic region (e.g., across the United States of America). In some examples, the record management endpoints 906 may support one or many facilities. The record management endpoints 906 include any suitable combination of software and/or hardware that are configured to provide management of dependent user records, authorized user practice management, and the like. The generation devices 908 may be any suitable device capable of generating messages within the record management endpoints 906, updating dependent records, collecting and processing imaging of dependent users, collecting and processing test results of dependent users, and the like.

At least a portion of the data generated by the generation devices 908 may be stored locally at the record management endpoints 906. Other portions of data may be collected by the transformative processing engine 108 and stored in the data warehouse 508. For example, the data from the generation devices 908 and/or the record management endpoints 906 may be streamed to the transformative processing engine 108 in one or more data streams, which may be integrated by the transformative processing engine 108 before being stored in the data warehouse 508.

Any suitable number of interceptors 910(1)-910(N) may be disposed throughout the architecture 900 to intercept messages and/or other communications that are sent between the record management endpoints 906, the transformative processing engine 108, and/or the data warehouse 508. For example, the interceptor 910(1) may be disposed in a network location between the record management endpoints 906 and the transformative processing engine 108, and the interceptor 910(N) may be disposed between the transformative processing engine 108 and the data warehouse 508. The interceptors 910 may include any suitable combination of software and/or hardware to facilitate interception of messages having certain data parameters. For example, the interceptors 910 may be busses that can deliver data to certain endpoints based on subscriptions. In this manner and as applicable to the techniques described herein, a subscription to one or more interceptors 910 can be made that identifies a particular dependent user or a set of dependent users (e.g., a complete set of dependent users for whom an organization is responsible) by respective dependent user identifiers. The interceptors 910 can scan messages to identify those that include the dependent user identifiers of interest. Some portion of these messages (e.g., a copy of some portion) can be added to a queue for later inspection or may be sent directly to the management system 902 for further processing. For example, such messages may include triggering information such as identify particular conditions of interest. In this manner, detection of the triggering information in the messages triggers commencement of a process of evaluating an authorized user model with respect to a condition associated with the individual identified in the message.

In addition to the management engine 904, the authorized user management system 902 also includes one or more databases including an authorized user model database 912 and a condition model database 914. The authorized user model database 912 may be used to store models of authorized users along with generic models. In some examples, the models of authorized users are unique to the respective authorized users, each representing a picture of all aspects of the authorized user's experience (e.g., credentials, on-the-job experience, and ongoing learning). The condition model database 914 may be used to store models of conditions of interest for evaluation. Initially, the condition model database 914 may include a small number of targeted conditions for evaluation, but the number of conditions may continue to grow as the management engine 904 is used to evaluate additional dependent user records. This may be possible because the management engine 904 includes a machine learning module that processes historical and/or current records of dependent users to build condition models (e.g., for a particular condition, what experience of authorized users is relevant for identifying and responding to the particular condition). The machine learning module may also process historical and/or current records of dependent users to build and/or enhance the authorized user models. In some examples, at least some form of the databases 912 and 914 are stored and/or replicated in the data warehouse 508.

The management architecture 900 also includes one or more consumption devices 916(1)-916(N). The consumption devices 916 may be any suitable devices including user devices such as mobile devices, laptop computers, desktop computers, tablets, streaming devices, wearable devices, and/or any other similar device. The consumption devices 916 may be configured to consume support elements generated by the management engine 904 and sent for presentation to the consumption devices 916. In some examples, the consumption devices 916 may be the same devices that are in the set of generation devices 908.

Figure 10:
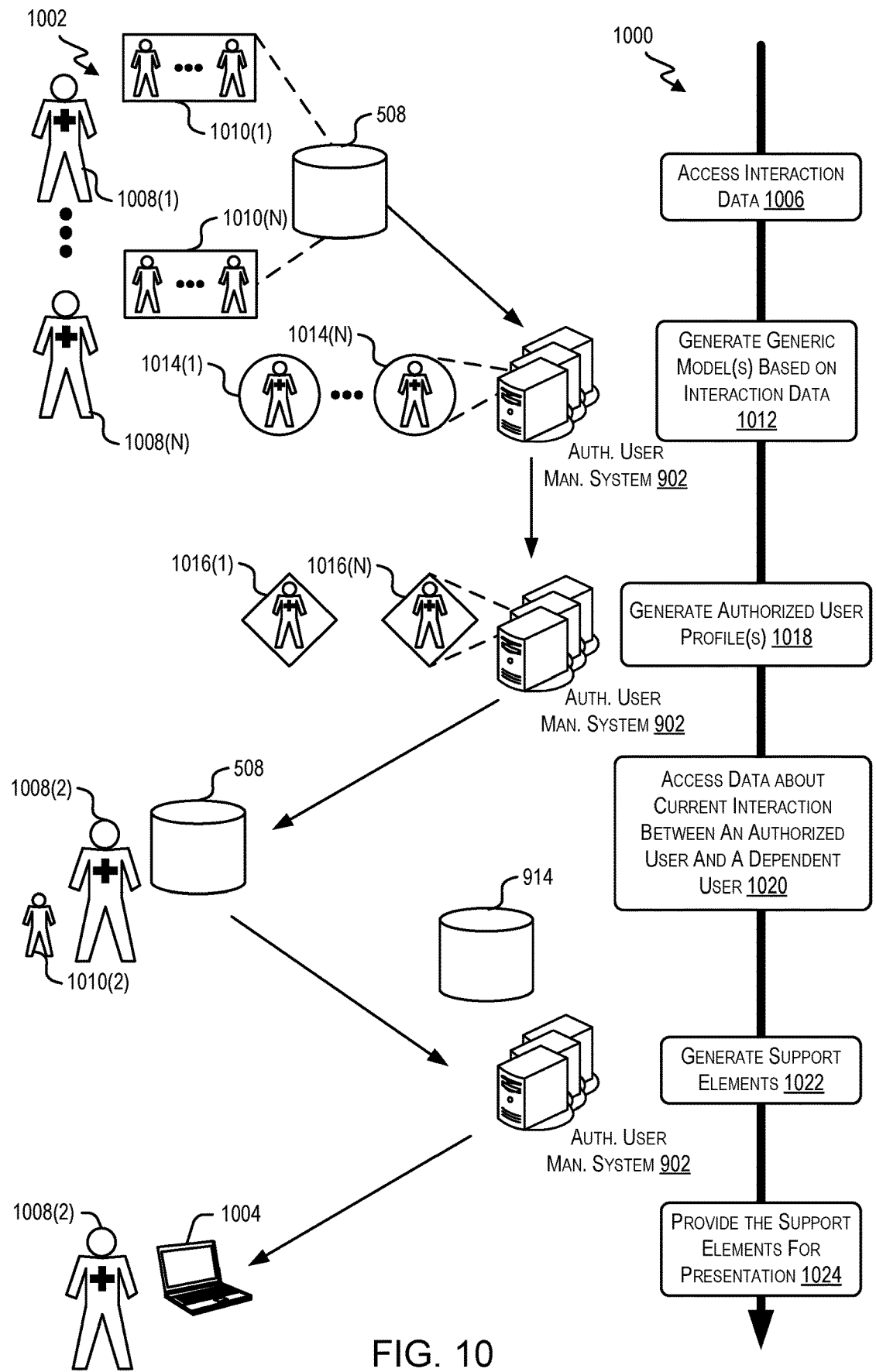
FIG. 10 is a simplified block diagram illustrating an example process for implementing techniques relating to data derived user behavior modeling, according to at least one example.

FIG. 10 illustrates a simplified block diagram 1002 depicting an example process 1000 in accordance with at least one example. The process 1000 is an example process for generating generic authorized user models, generating authorized user models, and generating support elements. The diagram 1002 depicts example states that correspond to the blocks of the process 1000. The diagram 1002 includes the authorized user management system 902, the data store 508 of the transformative processing engine 108, and a user device 1004 that perform at least a portion of the process 1000. The process 1000 begins at 1006 by accessing interaction data including condition data. The interaction data can include data that was previously collected by the transformative processing engine 108 and stored in the data store 508. The interaction data includes data collected about multiple authorized users 1008(1)-1008(N) who interacted with sets of dependent users 1010(1)-1010(N). For example, such data may identify conditions originally identified by the authorized users 1008, associated plans for responding to the conditions identified by the authorized users 1008, associated outcomes of the dependent users 1010 based on those plans, and other suitable information. In some examples, the interaction data may indicate not only historical interaction data, but may also include data sets describing an expected or desirable course of treatment based on a condition.

At 1012, the process 1000 generates generic model(s) 1014(1)-1014(N) based on the interaction data accessed at 1006. The authorized user management system 902 generates the generic model(s) 1014 at 1012. In some examples, the generic model(s) 1014 are used to predict how an authorized user should respond given certain conditions. These predictions can be output as decision support output, and when an authorized user model is considered, the decision support output can be tailored to the actual authorized user. Because the generic models 1014 are generated based on actual interaction data of real authorized users 1008 treating real dependent users 1010, the generic models 1014 can accurately follow actual practice habits of authorized users. The generic models 1014 can be adjusted, as described herein, to account for model outputs that are undesirable. For example, assume a generic model 1014, when evaluated, predicts that an authorized user 1008 perform action X. If it has recently been discovered that performance of action Y results in a better dependent user outcome, the generic model 1014 can be adjusted to account for this factor. In some examples, the generic models 1014 include a set of rules which is evaluated using input data (e.g., an authorized user model 1016) as part of generating decision support output. The generic models 1014 are generic in the sense that they generically represent authorized users 1008, but are not otherwise associated with a particular authorized user 1008. In some examples, the generic models 1014 include models that are particular to a practice specialty. The generic models 1014 can also be particular to a type of authorized user or based on an authorized user role. The generic models 1014 can also be particular to authorized users known to have different levels of experience. The generic models 1014 can be saved in any suitable data structure such as a computational format such as XML. The generic models 1014 can be stored in any suitable location after generation. For example, the generic models 1014 can be stored in the database 912.

At 1018, the process 1000 generates authorized user models(s) 1016(1)-1016(N). The authorized user management system 902 generates the authorized user models(s) 1016 at 1018. The authorized user models 1016 are particular to authorized users 1008 who are known to the authorized user management system 902. For example, the authorized users 1008 can be employees of a particular organization that operates the authorized user management system 902. In some examples, the authorized users 1008 are the same authorized users 1008 whose interaction data was accessed at 1006. In other examples, the authorized users 1008 for whom the authorized user models 1016 are generated do not come from the same group of authorized users whose interaction data was accessed at 1006. The authorized user models 1016, as described herein, include authorized user information, experience information, and the like that is descriptive of the authorized users 1008. In some examples, the authorized user models 1016 are instantiations of the generic models 1014. The authorized user models 1016 can be saved in any suitable data structure such as a computational format such as XML. The authorized user models 1016 can be stored in any suitable location after generation. For example, the authorized user models 1016 can be stored in the database 912.

Generating the authorized user models 1016 may be based on the generic models 1014 and/or may be generated without regard to the generic authorized user models. For example, in the first embodiment, if a new authorized user is added to the system and little to no historical data exists or is available for the new authorized user, a generic model 1014 may be relied upon to form a baseline for the new authorized user. The generic model 1014 can be selected to correspond to the credentials, experience, and other ongoing education the authorized user has obtained. In some examples, the generic model 1014 is selected based solely on the new authorized user's specialty and years of experience (e.g., family authorized user with 10 years of experience). In this example, generating the authorized user model 1016 may include copying an instantiation of the appropriate generic model 1014, assigning the instantiation to the new authorized user as her authorized user model 1016, and beginning to add any new experience, etc. to her authorized user model 1016 as it is recorded.

In some examples, the authorized user models 1016 are generated without regard to the generic models 1014. For example, data sources included information about an authorized user can be interrogated to obtain certain types of data relevant for building the authorized user model 1016. Such data may include a first set of data that includes credential data of the authorized user (e.g., age, degree, specialty, endorsements, years in practice, role, and any other suitable information indicative of credentials.). In some examples, this first set of data may be accessed from one or more record management endpoints 906 and/or from other locations. Such data may also include a second set of data that includes practice experience data of the authorized user (e.g., actual set of conditions the authorized user has responded to, what billing codes these conditions correspond to, orders placed, number of complications, identified conditions in labs, identified conditions in notes, and any other suitable information indicative of practice experience). In some examples, this second set of data may be accessed from one or more record management endpoints 906 and/or from other locations. Such data may also include a third set of data that includes ongoing education data of the authorized user (e.g., additional ongoing education that authorized user has obtained outside of her practice experience). In some examples, this third set of data may be accessed from one or more record management endpoints 906, accessed and/or derived from third-parties at which the authorized user has sought and/or read information relevant to their role, and/or received from the authorized user (e.g., after the user completes a program or reads a relevant article, she may make a note in a logging program).

At 1020, the process 1000 accesses data about current interactions between an authorized user 1008(2) and a dependent user 1010(2). The authorized user management system 902 accesses the data at 1018. The interactions include the authorized user 1008(2) responding to a one or more conditions of the dependent user 1010(2) during an office visit, on rounds, or otherwise. The data about current interactions can identify a condition for which the dependent user 1010(2) is being seen by the authorized user 1008(2). In some examples, the data about current interactions also includes dependent user record data, e.g., data from the dependent user 1010(2)'s electronic record (e.g., chart). The data accessed at 1020 can be used to provide a context in which the dependent user 1010(2) is interacting with the authorized user 1008(2).

In some examples, the data about the current interaction is obtained from the data warehouse 508, but may also be captured from one or more streams that include the interaction data. For example, updates to an electronic user record made by the authorized user 1008(2) following a visit with the dependent user 1010(2) can be accessed before they are stored in the data warehouse 508 (e.g., using one or more interceptors 910). In some examples, this data streamed via one or more data streams.

At 1022, the process 1000 generates support elements. The authorized user management system 902 generates the support elements based on a condition model accessed from the condition model database 914, an authorized user model 1016 accessed from the authorized user model database 912 and generated at 1018, and data about a current interaction, which may include one or more streamed messages that identify a likely present condition of the dependent user 1010(2). In some examples, generating the support elements includes comparing the authorized user model 1016 with the condition model to determine what support elements would be helpful for the authorized user 1008(2) given the condition and the current context of the dependent user 1010(2). In some examples, a condition preparedness score is computed by the authorized user management system 902 prior to generating the support elements, and the generation of the support elements is based on the condition experience score. The condition experience score attempts to approximate the level of experience an authorized user has with a certain condition. The condition is identified at 1020. The condition experience score can be compared to a set of experience thresholds to determine different sets of support elements. For example, for experience scores falling below a first threshold, more comprehensive sets of support elements will be generated (e.g., an order set, instructions for performing an evaluation, etc.) that are appropriate for authorized users with less experience treating the condition. For experience scores exceeding a second, higher threshold, less comprehensive sets of support elements will be generated (e.g., reminders, considerations, additional reading, etc.) that are appropriate for authorized users with more experience treating the condition. In some examples, the authorized users 1008 are bucketized (e.g., inexperienced, moderately experienced, very experienced, expert, etc.) based on the comparison with the condition model, and the support elements correspond to whichever bucket the authorized user 1010 is placed in.

At 1024, the process 1000 provides the support elements for presentation. The authorized user management system 902 provides the support elements at 1024 for presentation at the user device 1004. The user device 1004 is accessible by or otherwise associated with the authorized user 1008(2). For example, the user device 1004 can be used by the authorized user 1008(2) to manage aspects of her practice within an existing management application, and the support elements can be presented in a window within the management application. The intrusiveness and engagement required for dismissal of the support elements depends, in some examples, on the condition preparedness score. For example, for preparedness scores falling below a first threshold, sets of support elements will be presented in a more intrusive manner. For preparedness scores exceeding a second, higher threshold, sets of support elements will be presented in a less intrusive manner. This may function to ensure that the appropriate amount of attention is given by authorized users to support elements. The support elements can be presented at any suitable user device including, for example, mobile phones, laptops, terminals, smart watches, and the like. The format of the support elements can be adjusted to account for the receiving device and the method by which they will be transmitted. For example, instead of or in addition to the support elements being provided within a management application, support elements can be appropriately formatted and sent via Short Messaging Service (SMS) and other text-message based systems, instant messaging, email, real-time text, and the like.

Figure 11:
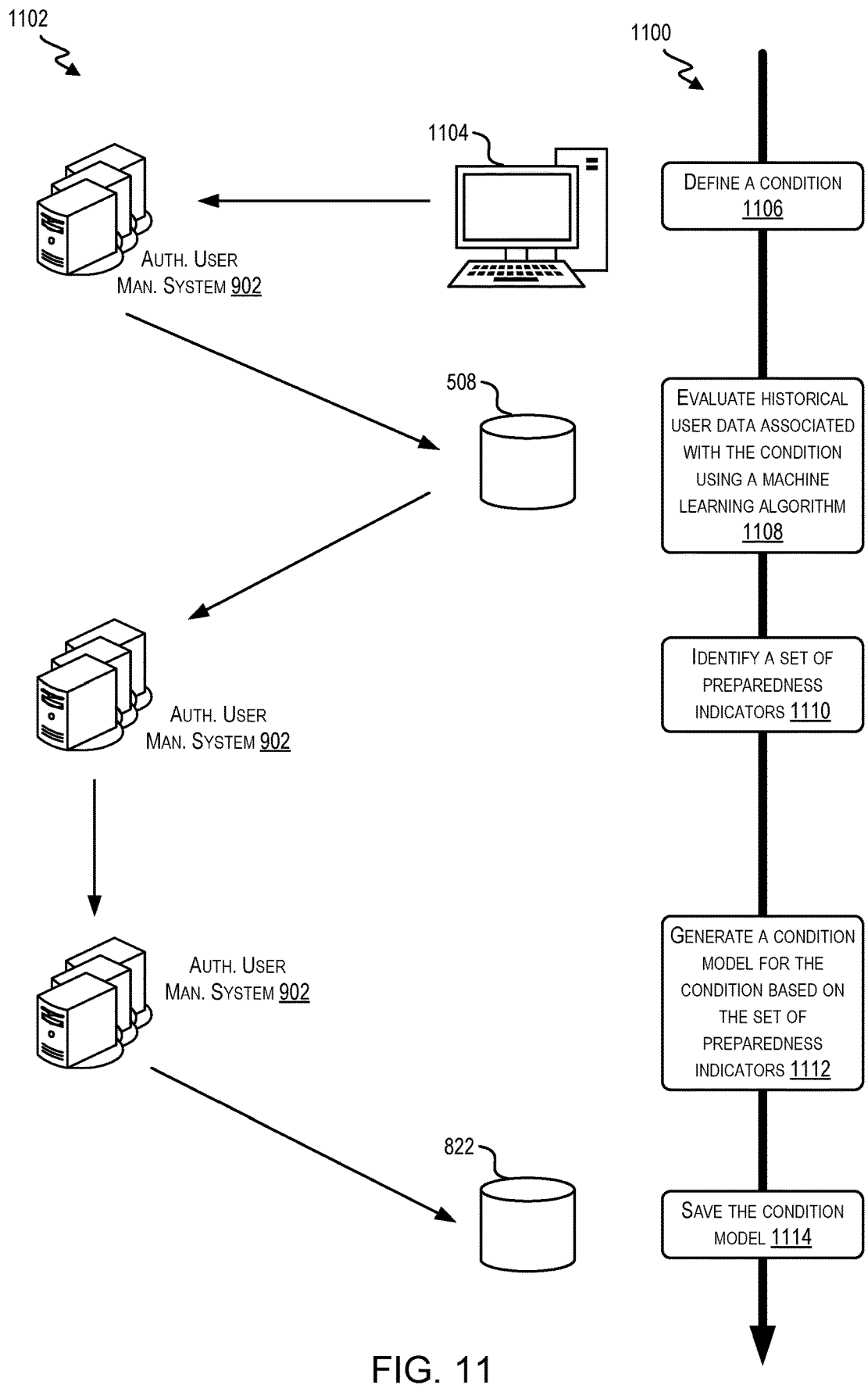
FIG. 11 is a simplified block diagram illustrating an example process for implementing techniques relating to data derived user behavior modeling, according to at least one example.

FIG. 11 illustrates a simplified block diagram 1102 depicting an example process 1100 in accordance with at least one example. The process 1100 is an example process for generating condition models. The diagram 1102 depicts example states that correspond to the blocks of the process 1100. The diagram 1102 includes the authorized user management system 902, the data warehouse 508, the condition model database 914, and a user device 1104 (e.g., the consumption device 916) that perform at least a portion of the process 1100. The process 1100 begins at 1106 by defining a condition. This may include a user using the user device 1104 to select which conditions should be monitored by the system and which conditions will function as triggers, as described herein. In some examples, a targeted set of conditions can be defined (e.g., those that are difficult to identify, difficult to respond to, occur frequently, and/or based on other characteristics). Defining the condition may include defining which data parameters are relevant for condition (e.g., parameters in the records of dependent users). For example, for some conditions, measured lab values may be more important observed vital values. For some conditions, the condition may correspond to a diagnosis, but, in other examples, the condition itself may be defined as a change in some parameter in the record, even when a diagnosis is unknown.

At 1108, the process 1100 includes evaluating historical user data associated with the condition using a machine learning algorithm. This can be performed by the authorized user management system 902 accessing the data warehouse 508. For example, the data in the data warehouse 508 can be used to train a machine learning model to determine which features in the data correspond most to the condition at issue. In this manner, the system can determine which features in the data are important to consider and which can be ignored. In some examples, 1108 can be performed manually and/or without the assistance of the machine learning algorithm. For example, a knowledgeable professional can define which data is relevant.

At 1110, the process 1100 includes identifying a set of preparedness indicators. This can be performed by the authorized management system 902. In some examples, identifying the set of preparedness indicators is performed based on output from 1108. For example, the set of preparedness indicators can correspond to the parameters identified at 1108, and represent what types of knowledge or experience is necessary for responding to the condition. In a particular example, the set of preparedness indicators may indicate that a certain condition should only be treated by a specialist, unless the authorized user in question has encountered a similar condition more than 20 times in the last five years. Thus, the preparedness indicators may be formulated as a set of Boolean rules with ranges, values, and the like to define what type of preparation is necessary to respond to the condition at issue.

At 1112, the process 1100 includes generating a condition model for the condition based on the set of preparedness indicators. This is performed by the authorized user management system 902. This may include using the set of preparedness indicators as parameters in the condition model. In some examples, a condition model can be generated for each condition, for a class of conditions, and for any other variation between a lab value and registered diagnosis.

At 1114, the process 1100 includes saving the condition model. This is performed by the authorized user management system 902. This may include saving the condition model in the condition model database 914. The condition model may be saved in a computational format to enable comparison with the authorized user model, which may also be saved in a computational format.

FIG. 12 illustrates an example authorized user model 1016 in accordance with at least one example. The authorized user model 1016 belongs to Mr. Wilson. The authorized user model 1016 can be organized in any suitable format such as, for example, Extensible Markup Language (XML), or other computational format. The authorized user model 1016 includes demographic information 1202 (e.g., generic data objects), experience information 1204 (e.g., experience data objects), and activity information 1206 (e.g., activity data objects). The demographic information 1202 indicates basic information about the authorized user (e.g., specialty, years in practice, location, and other similar information). The experience information 1204 indicates information about the authorized user's experience with certain conditions (e.g., condition frequency, condition severity, outcomes related to treatment of conditions, and other similar information). The activity information 1206 indicates information about activities performed by the authorized user and detected by the system (e.g., CME course completed, articles read, consultations, and any other suitable information). The authorized user model 1016 is updated as the authorized user obtains additional experience and otherwise interacts with the system.

Figure 13:
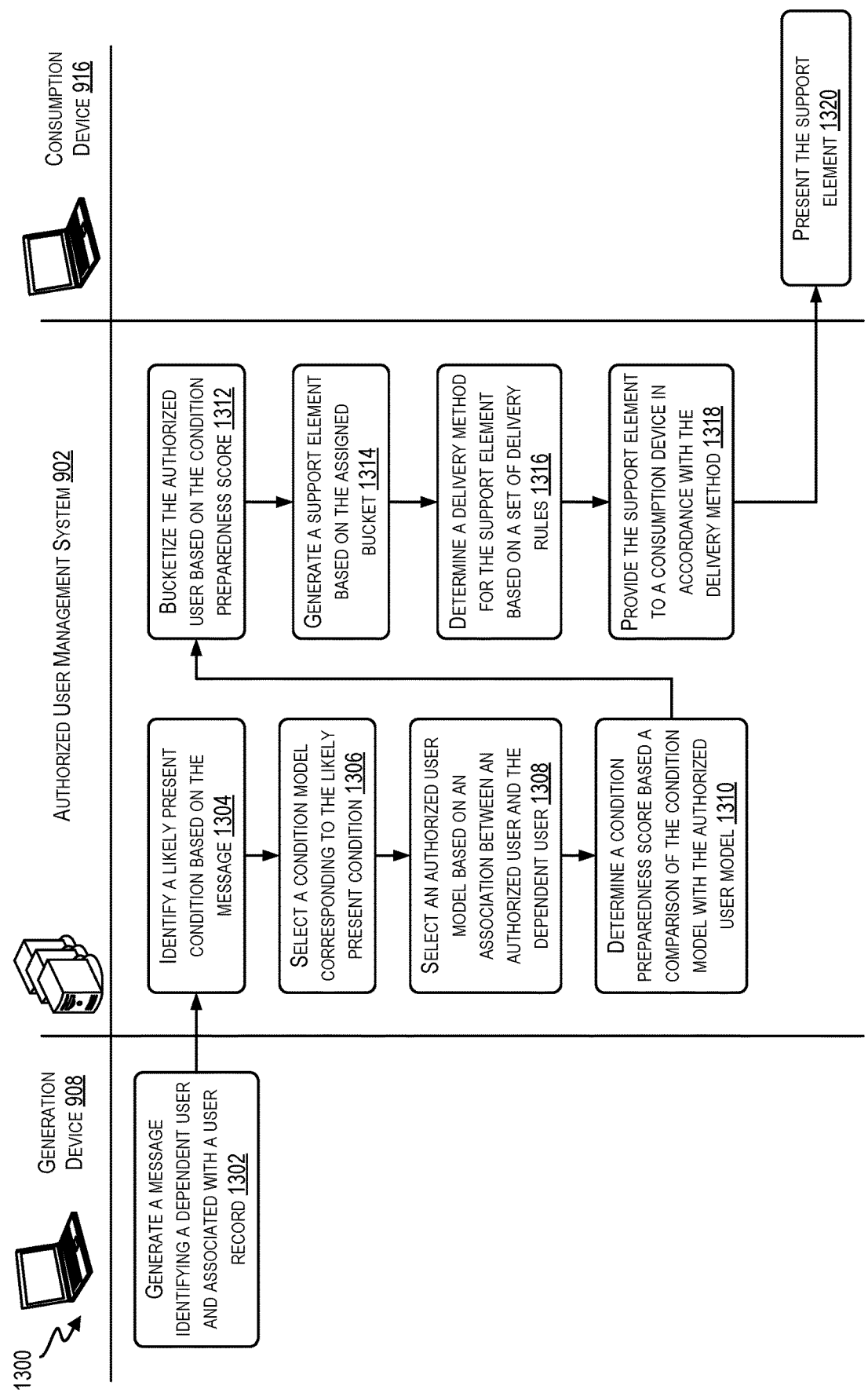
FIG. 13 is a flow chart illustrating an example process for implementing techniques relating to data derived user behavior modeling, according to at least one example.
Figure 14:
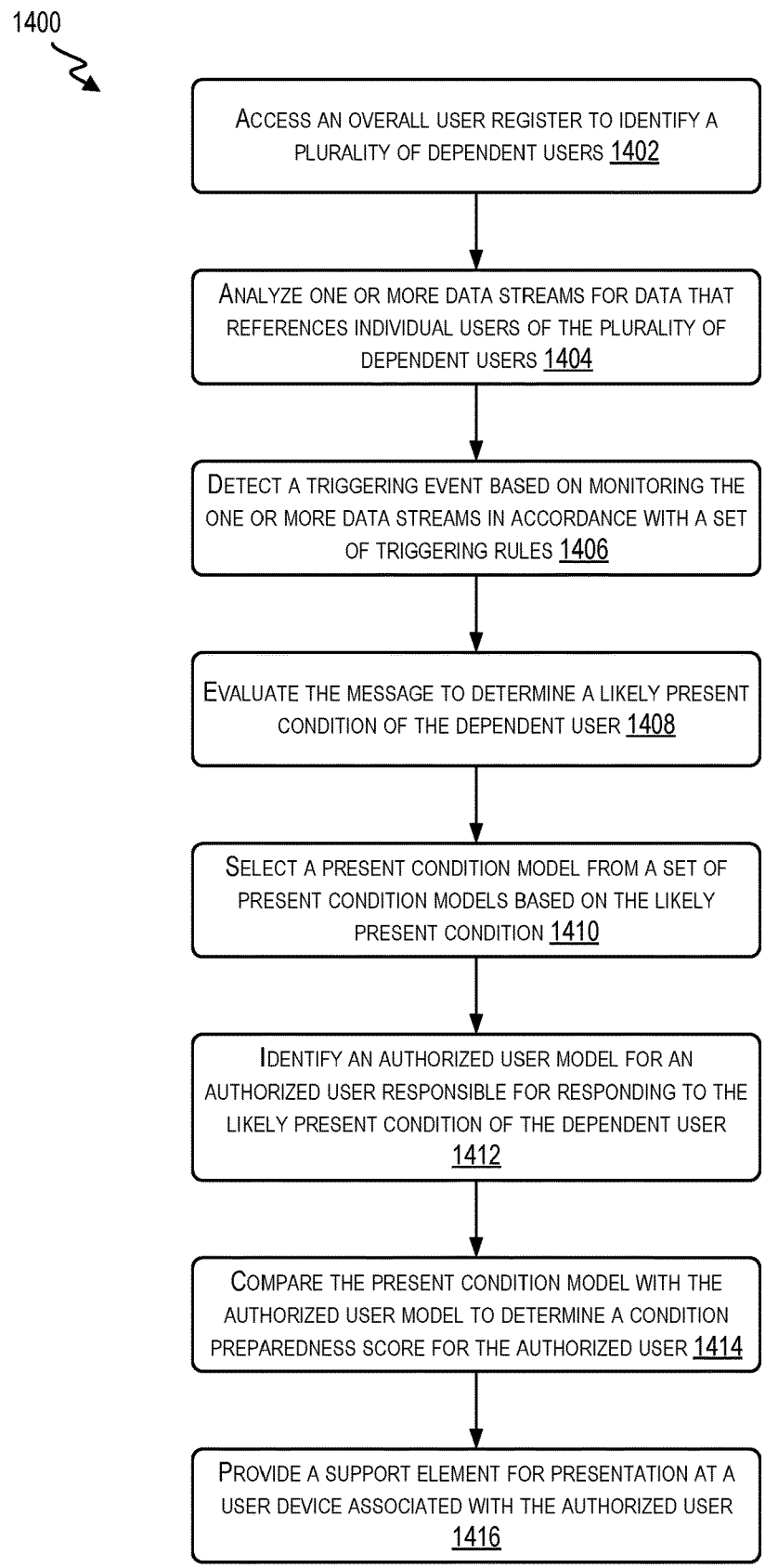
FIG. 14 is a flow chart illustrating an example process for implementing techniques relating to data derived user behavior modeling, according to at least one example.

FIGS. 13 and 14 illustrate example flow diagrams showing respective processes 1300 and 1400 as described herein. These processes 1300 and 1400 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

FIG. 13 illustrates the process 1300 including example acts or techniques relating to data derived user behavior modeling, according to at least one example. The management engine 904 within the authorized user management system 902, a generation device 908, and/or a consumption device 916 performs the process 1300 of FIG. 13.

The process 1300 begins at 1302 by generating a message identifying a dependent user and associated with a user record. In some examples, this is performed by the generation device 908 (FIG. 9). For example, a user may use the generation device 908 to take some action with respect to the dependent user and/or her user record. This action may cause the message to be generated (e.g., any suitable message including those defined by the HL7 format). In some examples, the generation device 908 can include a machine (e.g., medical equipment) that automatically generates the message in response to some condition being fulfilled, test taken, and the like. For example, results from a test administered to the dependent user can be included in the message. The messages may function to update the user record (e.g., add data to the user record, remove data from the user record, and/or revise data in the user record).

At 1304, the process 1300 includes identifying a likely present condition based on the message. This is performed by the authorized user management system 902. Identifying the likely present condition can include scanning the message to identify structured and/or unstructured data that identifies some predefined condition. For example, an input note may identify the condition, a recorded value may be the condition, etc. In this manner, the identifying at 1304 may function to trigger the remaining portion of the process 1300. In some examples, a header portion of the message, which may be based on the HL7 or other industry standard, may identify the dependent user and a message type. Based on this information, the authorized user management system 902 may be informed as to what types of potential conditions may be present in the content of the message. In this manner, the message type may be used to determine whether to evaluate the message and, if so, how to efficiently evaluate the message (e.g., what to look for in the message). The message may correspond to the interaction data described herein.

At 1306, the process 1300 includes selecting a condition model corresponding to the likely present condition. This is performed by the authorized user management system 902. In some examples, the authorized user management system 902 is used to manage a plurality of condition models for various conditions, classes of conditions, and the like. At 1306, the process decides which condition model should be used for generating the support elements. In some examples, this selection is straightforward (e.g., a condition model exists that maps directly to the likely present condition). In other examples, the system determines a model that is most closely related to the likely present condition. For example, this can include selection of a model that is generic for a type of conditions when the likely present condition is a species of the type.

At 1308, the process 1300 includes selecting an authorized user model based on an association an association between the authorized user and the dependent user. This is performed by the authorized user management system 902. This can include accessing a directory in which dependent users and authorized users are associated. For example, the organization that facilities care for the dependent users may as a matter of course maintain a directory that assigns a group of authorized users to the dependent user. In some examples, the message may be processed to identify the authorized user. For example, the message may identify the dependent user and that the authorized user that is responsible for the dependent user. Once the association has been determined, the authorized user model for the appropriate authorized user is selected. For example, the authorized user model can be accessed from a storage location.

At 1310, the process 1300 includes determining a condition preparedness score based on a comparison of the condition model with the authorized user model. This is performed by the authorized user management system 902. As both the condition model and the authorized user model can be prepared in a computational format, this comparison can include evaluating the authorized user model with respect to the condition model. This comparison will reveal which preparedness indicators defined in the condition model have triggered in the authorized user model. As each preparedness indicators may be weighted, depending on which indicators trigger will impact the condition preparedness score. For example, one preparedness indicator may require education on the condition, while another may require recent experience with the condition. In this example, the second indicator may have a greater weight than the first. In this manner, the model may be biased towards certain types of preparedness over others. In some examples, the condition preparedness score is represented as an integer that includes digits that correspond to which indicators triggered. In some examples, each indicator may be assigned as sub score that totals some fixed number (e.g., 100). In this example, determining the condition preparedness score may include adding the scores for those indicators that triggered. In other examples, the condition preparedness score may take into account relationships between indicators that triggered. For example, when a first indicator triggers in connection with a second indicator, the score assigned to the first indicator may be greater than if the first indicator triggered on its own (e.g., without the second indicator triggering).

At 1312, the process 1300 includes bucketizing the authorized user based on the condition preparedness score. This is performed by the authorized user management system 902. In some examples, the buckets can be divided by percentiles. In other examples, the buckets can be divided by percentages (e.g., top 25%, middle upper 25%, middle lower 25%, and lower 25%). In some examples, the buckets can be defined in any other suitable manner. For example, the condition preparedness score may itself define which bucket the authorized user is assigned.

At 1314, the process 1300 includes generating a support element based on the assigned bucket. This is performed by the authorized user management system 902. In some examples, the support elements are preassigned to the buckets. In this manner, once the authorized user is assigned to a bucket, the support element may be selected based on an association between the bucket and the support element. In other examples, generating the support element may include accessing a set of support element artifacts associated with the bucket and/or the score associated with the bucket.

At 1316, the process 1300 includes determining a delivery method for the support element based on a set of delivery rules. This is performed by the authorized user management system 902. In some examples, the delivery rules may include conditional statements or other suitable rule statements that define, based on the support element, the delivery method. For example, depending on the type of support element, the delivery method may be more intrusive or less intrusive. In some examples, the delivery method can include sending via SMS, sending via notifications in an application, sending via other appropriate delivery methods, and in any other appropriate method.

At 1318, the process 1300 includes providing the support element to a consumption device in accordance with the delivery method. This is performed by the authorized user management system 902.

At 1320, the process 1300 includes presenting the support element. This is performed by the consumption device 916 (FIG. 9). Presenting the support element can include presenting the support element in a manner that is considerate of the condition preparedness score and/or the assigned bucket. For example, more intrusive support elements may be presented in a first manner while less intrusive support elements may be presented in a second manner.

FIG. 14 illustrates the process 1400 including example acts or techniques relating to data derived user behavior modeling, according to at least one example. The management engine 904 within the authorized user management system 902 performs the process 1400 of FIG. 14.

The process 1400 begins at 1402 by accessing an overall user register, and/or other data structure that stores information about the dependent users, to identify a plurality of dependent users. This is performed by the management engine 904 (FIG. 9) of the authorized user management system 902 (FIG. 9).

At 1404, the process 1400 includes analyzing one or more data streams for data that references individual dependent users of the plurality of dependent users. This is performed by the management engine 904 of the authorized user management system 902. The one or more data streams can extend between a plurality of generation devices and one more storage devices. In some examples, at least one data stream includes messages of a standardized format (e.g., HL7 format).

At 1406, the process 1400 includes detecting a triggering event based on monitoring the one or more data streams in accordance with a set of triggering rules. This is performed by the management engine 904 of the authorized user management system 902. The triggering event includes a message that updates a user record associated with a dependent user of the plurality of dependent users.

At 1408, the process 1400 includes evaluating the message to determine a likely present condition of the dependent user. This is performed by the management engine 904 of the authorized user management system 902. In some examples, the evaluation is based on one or more condition data present in the message or in the user record. The evaluation may consider structured data in the message and/or unstructured data. For example, the evaluating may be performed using a natural language processing engine to review the unstructured data for identification of the likely present condition. When more than one condition is detected, portions of the process 1400 may be performed in parallel to generate support elements to address the other conditions.

At 1410, the process 1400 includes selecting a present condition model from a set of present condition models based on the likely present condition. This is performed by the management engine 904 of the authorized user management system 902. The present condition model includes a set preparedness indicators indicative of authorized user preparedness for responding to the likely present condition.

At 1412, the process 1400 includes identifying an authorized user model for an authorized user responsible for responding to the likely present condition of the dependent user. This is performed by the management engine 904 of the authorized user management system 902. The authorized user model may include a plurality of data objects representative of user preparedness for responding to the likely present condition. The plurality of data objects can include generic data objects, experience data objects, and activity data objects. The generic data objects represent generic aspects of the authorized user. The experience data objects represent historical experience the authorized user has obtained by responding to the likely present condition at other times. The activity data object represents historical knowledge the authorized user has obtained that is related to the likely present condition. The experience data objects are determined based on one or more historical data sources including a code-based data source, a note entry data source, or a placed order data source.

At 1414, the process 1400 includes comparing the present condition model with the authorized user model to determine a condition preparedness score for the authorized user. This is performed by the management engine 904 of the authorized user management system 902.

At 1416, the process 1400 includes providing a support element for presentation at a user device associated with the authorized user. This is performed by the management engine 904 of the authorized user management system 902. In some examples, this is based on the condition preparedness score. In some examples, the support element includes a communication that is tailored to context of the authorized user with respect to the dependent user.

In some examples, the process 1400 further includes assigning the authorized user to one of a plurality of designations based on the condition preparedness score (e.g., buckets). In this example, each designation represents a distinct level of authorized user preparedness for responding to the likely present condition. The process 1400 further includes generating the support element based on the assigned designation.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps, and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method, comprising:
  accessing, from an interaction data database and by a centralized server, historical interaction data identifying historical interactions of a set of authorized users with sets of support elements previously presented to the set of authorized users, the sets of support elements previously generated in part based on data collected from a clinical data warehouse associated with the centralized server and a first set of authorized user profiles belonging to the set of authorized users, the set of support elements comprising sets of tasks for consideration by individual authorized users of the set of authorized users as part of responding to present conditions of dependent users;
  determining, from the historical interaction data, first tasks of the set of tasks performed by the individual authorized users;
  determining, from the historical interaction data, second tasks of the set of tasks not performed by the individual authorized users;
  accessing a predictive model to which authorized user profiles are compared to generate the sets of support elements, the predictive model comprising a set of weighted values;
  updating at least one weighted value of the predictive model based on at least one of the first tasks or the second tasks;
  generating a second set of authorized user profiles based on the predictive model including the updated at least one weighted value; and
  storing the second set of authorized user profiles.

2. The computer-implemented method of claim 1, wherein the set of support elements are embodied in electronic communications that are customized to contexts of the set of authorized users with respect to the dependent users.

3. The computer-implemented method of claim 1, wherein each support element is capable of being presented at a user device associated with a respective authorized user, each support element comprising one or more items retrieved from a database associated with the centralized server.

4. The computer-implemented method of claim 1, wherein each authorized user model comprises a plurality of data objects representative of user preparedness for responding to at least one present condition, the plurality of data objects comprising at least one of a generic data object, an experience data object, or an activity data object.

5. The computer-implemented method of claim 4, wherein:
the generic data object represents generic information of each authorized user;
the experience data object represents historical experience each authorized user has obtained by responding to the at least one present condition at other times; and
the activity data object represents additional knowledge each authorized user has obtained that is related to the at least one present condition.

6. The computer-implemented method of claim 1, wherein determining, from the historical interaction data, the first tasks of the set of tasks performed by the individual authorized users comprises identifying trends in the historical interaction data relating to performance of the set of tasks.

7. The computer-implemented method of claim 1, wherein the weighted values correspond to characteristics of at least one of the set of authorized users or the present conditions.

8. The computer-implemented method of claim 1, wherein storing the second set of authorized user profiles comprises storing the second set of authorized user profiles in a profile database associated with the centralized server.

9. The computer-implemented method of claim 8, further comprising, for a particular dependent user of the dependent users, performing by the centralized server:
detecting a triggering event based on monitoring one or more data streams in accordance with a set of triggering rules, the triggering event comprising a message that updates a user record associated with the particular dependent user;
determining a likely present condition of the particular dependent user based on one or more condition data present in the message or in the user record;
selecting a present condition model from a set of present condition models stored on the centralized server based on the likely present condition;
identifying a particular authorized user model from the second set of authorized user models, the particular authorized user model belonging to a particular authorized user that is associated with the particular dependent user;
comparing the present condition model with the particular authorized user model to determine a condition preparedness score for the particular authorized user;
generating, based on the condition preparedness score, a support element capable of being presented at a user device associated with the particular authorized user; and
transmitting the support element to the user device for presentation at the user device.

10. The computer-implemented method of claim 1, further comprising:
generating, based on a particular authorized user profile of the second set of authorized user profiles, a support element capable of being presented at a user device associated with a particular authorized user with whom the particular authorized user profile is associated; and
transmitting the support element to the user device for presentation at the user device.

11. The computer-implemented method of claim 1, further comprising collecting historical experience data identifying experience events of the individual authorized users with respect to experience pertaining to responding to the present conditions, and wherein updating the at least one weighted value of the predictive model is further based at least in part on the historical experience data.

12. The computer-implemented method of claim 1, further comprising:
receiving, from a user device associated with a particular authorized user, a first request to view a first authorized user profile of the first authorized user profiles, the first authorized user profile associated with the particular authorized user;
responsive to the first request, providing a first view of a graphical user interface for presentation at the user device, the first view presenting information about the first authorized user profile; and
after storing the second set of authorized user profiles, updating the graphical user interface to present a second view of the graphical user interface, the second view presenting information about a second authorized user profile of the second authorized user profiles, the second authorized user profile associated with the particular authorized user.

13. A centralized server system, comprising:
one or more data storage devices comprising a clinical data warehouse;
a memory comprising computer-executable instructions; and
a processor configured to access the memory and execute the computer-executable instructions to at least:
access historical interaction data identifying historical interactions of a set of authorized users with sets of support elements previously presented to the set of authorized users, the sets of support elements previously generated in part based on data collected from the clinical data warehouse associated with the centralized server system and a first set of authorized user profiles belonging to the set of authorized users, the set of support elements comprising sets of tasks for consideration by individual authorized users of the set of authorized users as part of responding to present conditions of dependent users;
determine, from the historical interaction data, first tasks of the set of tasks performed by the individual authorized users;
determine, from the historical interaction data, second tasks of the set of tasks not performed by the individual authorized users;
access a predictive model to which authorized user profiles are compared to generate the sets of support elements, the predictive model comprising a set of weighted values;
update, at least one weighted value of the predictive model based on at least one of the first tasks or the second tasks;

generate a second set of authorized user profiles based on the predictive model including the updated at least one weighted value; and store the second set of authorized user profiles in the one or more data storage devices.

14. The centralized server system of claim 13, wherein each support element is capable of being presented at a user device associated with a respective authorized user, each support element comprising one or more items retrieved from the one or more data storage devices.

15. The centralized server system of claim 13, wherein each authorized user model comprises a plurality of data objects representative of user preparedness for responding to at least one present condition, the plurality of data objects comprising at least one of a generic data object, an experience data object, or an activity data object.

16. The centralized server system of claim 13, wherein determining, from the historical interaction data, the first tasks of the set of tasks performed by the individual authorized users comprises identifying trends in the historical interaction data relating to performance of the set of tasks.

17. A non-transitory computer-readable storage device comprising computer-executable instructions that, when executed by one or more computer systems, cause the one or more computer systems to perform operations comprising:

accessing, from a interaction data database and by a centralized server, historical interaction data identifying historical interactions of a set of authorized users with sets of support elements previously presented to the set of authorized users, the sets of support elements previously generated in part based on data collected from a clinical data warehouse associated with the centralized server and a first set of authorized user profiles belonging to the set of authorized users, the set of support elements comprising sets of tasks for consideration by individual authorized users of the set of authorized users as part of responding to present conditions of dependent users;

determining, from the historical interaction data, first tasks of the set of tasks performed by the individual authorized users;

determining, from the historical interaction data, second tasks of the set of tasks not performed by the individual authorized users;

accessing a predictive model to which authorized user profiles are compared to generate the sets of support elements, the predictive model comprising a set of weighted values;

updating, at least one weighted value of the predictive model based on at least one of the first tasks or the second tasks;

generating a second set of authorized user profiles based on the predictive model including the updated at least one weighted value; and storing the second set of authorized user profiles.

18. The non-transitory computer-readable storage device of claim 17, wherein the weighted values correspond to characteristics of at least one of the set of authorized users or the present conditions.

19. The non-transitory computer-readable storage device of claim 17, wherein the operations further comprise:

receiving, from a user device associated with a particular authorized user, a first request to view a first authorized user profile of the first authorized user profiles, the first authorized user profile associated with the particular authorized user;

responsive to the first request, providing a first view of a graphical user interface for presentation at the user device, the first view of the graphical user interface presenting information about the first authorized user profile; and after storing the second set of authorized user profiles, updating the graphical user interface to present a second view of the graphical user interface, the second view of the graphical user interface presenting information about a second authorized user profile of the second authorized user profiles, the second authorized user profile associated with the particular authorized user.

20. The non-transitory computer-readable storage device of claim 17, wherein the operations further comprise collecting historical experience data identifying experience events of the individual authorized users with respect to experience pertaining to responding to the present conditions, and wherein updating the at least one weighted value of the predictive model is further based at least in part on the historical experience data.

* * * * *